(12) United States Patent
Chen et al.

(10) Patent No.: US 12,191,007 B2
(45) Date of Patent: Jan. 7, 2025

(54) HUMAN-IN-THE-LOOP INTERACTIVE MODEL TRAINING

(71) Applicant: Google LLC, Mountain View, CA (US)

(72) Inventors: Kai Chen, San Bruno, CA (US); Eyal Oren, Los Gatos, CA (US); Hector Yee, Mountain View, CA (US); James Wilson, Littleton, MA (US); Alvin Rajkomar, Mountain View, CA (US); Michaela Hardt, Mountain View, CA (US)

(73) Assignee: Google LLC, Mountain View, CA (US)

( * ) Notice: Subject to any disclaimer, the term of this patent is extended or adjusted under 35 U.S.C. 154(b) by 1261 days.

(21) Appl. No.: 16/618,656

(22) PCT Filed: Sep. 29, 2017

(86) PCT No.: PCT/US2017/054213
§ 371 (c)(1),
(2) Date: Dec. 2, 2019

(87) PCT Pub. No.: WO2019/045758
PCT Pub. Date: Mar. 7, 2019

(65) Prior Publication Data
US 2021/0358579 A1  Nov. 18, 2021

Related U.S. Application Data

(60) Provisional application No. 62/552,088, filed on Aug. 30, 2017.

(51) Int. Cl.
*G16H 10/60* (2018.01)
*G06N 20/00* (2019.01)

(52) U.S. Cl.
CPC ............. *G16H 10/60* (2018.01); *G06N 20/00* (2019.01)

(58) Field of Classification Search
CPC ...... G06F 7/00; G06F 15/18; G06F 17/30339; G06F 17/30625; G06N 20/00;
(Continued)

(56) References Cited

U.S. PATENT DOCUMENTS 7,752,152 B2   7/2010 Paek et al.
7,958,113 B2 *  6/2011 Fan .................. G06F 16/24545
                                                  707/718
(Continued)

OTHER PUBLICATIONS

Duch, Wlodzislaw, Rafal Adamczak, and Krzysztof Grabczewski. "A new methodology of extraction, optimization and application of crisp and fuzzy logical rules." IEEE Transactions on Neural Networks 12.2 (2001): 277-306. (Year: 2001).*

(Continued)

*Primary Examiner* — Randall K. Baldwin
(74) *Attorney, Agent, or Firm* — McDonnell Boehnen Hulbert & Berghoff LLP

(57) ABSTRACT

Example embodiments relate to a method for training a predictive model from data. The method includes defining a multitude of predicates as binary functions operating on time sequences of the features or logical operations on the time sequences of the features. The method also includes iteratively training a boosting model by generating a number of new random predicates, scoring all the new random predicates by weighted information gain with respect to a class label associated with a prediction of the boosting model, selecting a number of the new random predicates with the highest weighted information gain and adding them to the boosting model, computing weights for all the predicates in the boosting model, removing one or more of the selected new predicates with the highest information gain from the boosting model in response to input from an operator. The method may include repeating the prior steps a plurality of times.

33 Claims, 15 Drawing Sheets

(58) Field of Classification Search
CPC ........ G06N 20/20; G06N 3/0427; G06N 3/08; G06N 5/003; G06N 5/022; G06N 5/045; G06N 99/005; G16H 10/60; G06G 7/00; G10L 15/183
See application file for complete search history.

(56) References Cited

U.S. PATENT DOCUMENTS

| | | | |
|---|---|---|---|
| 9,092,979 | B2 | 7/2015 | Burry et al. |
| 9,223,833 | B2 | 12/2015 | Lightner et al. |
| 2008/0147574 | A1* | 6/2008 | Chidlovskii ............ G06F 16/35 706/12 |
| 2008/0168011 | A1* | 7/2008 | Steinberg ............ G06F 16/2365 706/12 |
| 2008/0222093 | A1* | 9/2008 | Fan ................... G06F 16/24545 |
| 2013/0346351 | A1 | 12/2013 | Lin et al. |
| 2015/0379429 | A1* | 12/2015 | Lee .......................... G09B 5/00 706/11 |
| 2016/0025896 | A1 | 1/2016 | Rose et al. |
| 2016/0078361 | A1* | 3/2016 | Brueckner .............. H04L 67/10 706/12 |
| 2016/0162458 | A1 | 6/2016 | Munro et al. |
| 2016/0364876 | A1 | 12/2016 | Lackey et al. |
| 2017/0098172 | A1 | 4/2017 | Ellenbogen et al. |
| 2017/0193118 | A1 | 7/2017 | Pratt |
| 2019/0370605 | A1* | 12/2019 | Xie ..................... G06F 18/2148 |

OTHER PUBLICATIONS

D'Acierno, Antonio, Massimo Esposito, and Giuseppe De Pietro. "An extensible six-step methodology to automatically generate fuzzy DSSs for diagnostic applications." BMC bioinformatics 14.1 (2013): 1-19. (Year: 2013).*
Um, Ashwin kumar, and Ananda kumar KR. "Data Preparation by CFS: An Essential Approach for Decision Making Using C 4.5 for Medical Data Mining." 2013 Third International Conference on Advanced Computing and Communication Technologies (ACCT). IEEE, 2013: 77-85. (Year: 2013).*
Rios, Anthony, and Ramakanth Kavuluru. "Supervised extraction of diagnosis codes from EMRs: role of feature selection, data selection, and probabilistic thresholding." 2013 IEEE International Conference on Healthcare Informatics. IEEE, 2013: 66-73. (Year: 2013).*
D'Souza, Jennifer, and Vincent Ng. "Knowledge-rich temporal relation identification and classification in clinical notes." Database 2014 (2014): 1-20. (Year: 2014).*
Mihăilă, Claudiu, and Sophia Ananiadou. "Semi-supervised learning of causal relations in biomedical scientific discourse." Biomedical engineering online 13.2 (2014): 1-24. (Year: 2014).*
Holzinger, Andreas. "Interactive machine learning for health informatics: when do we need the human-in-the-loop?." Brain Informatics 3.2 (2016): 119-131. (Year: 2016).*
Kovalerchuk, Boris, Evgenii Vityaev, and Husan Yusupov. "Symbolic methodology in numeric data mining: relational techniques for financial applications." arXiv preprint cs/0208022 (2002): 1-20 (Year: 2002).*
Duch, Wlodzislaw, Rudy Setiono, and Jacek M. Zurada. "Computational intelligence methods for rule-based data understanding." Proceedings of the IEEE 92.5 (2004): 771-805. (Year: 2004).*
Liu, Bing, et al. "Text classification by labeling words." Aaai. vol. 4. 2004. (Year: 2004).*
Syarif, Iwan, et al. "Application of bagging, boosting and stacking to intrusion detection." Machine Learning and Data Mining in Pattern Recognition: 8th International Conference, MLDM 2012, Berlin, Germany, Jul. 13-20, 2012. Proceedings 8. Springer Berlin Heidelberg, 2012. (Year: 2012).*
Batal, Iyad, et al. "Mining recent temporal patterns for event detection in multivariate time series data." Proceedings of the 18th ACM SIGKDD international conference on Knowledge discovery and data mining. 2012. (Year: 2012).*
Um, Ashwin kumar, and Ananda kumar KR. "Data Preparation by CFS: An Essential Approach for Decision Making Using C 4.5 for Medical Data Mining." 2013 Third International Conference on Advanced Computing and Communication Technologies (ACCT). IEEE, 2013: 78-85 (Year: 2013).*
Hu, Yuening, et al. "Interactive topic modeling." Machine learning 95 (2014): 423-469. (Year: 2014).*
Luo, Gang. "PredicT-ML: a tool for automating machine learning model building with big clinical data." Health Information Science and Systems 4 (2016): 1-16. (Year: 2016).*
Lipton, Z. C. The Mythos of Model Intepretability, arXiv:1606.03490 [cs.LG] (Jun. 2016).
Holzinger, A. "Interactive machine learning for health informatics: when do we need human in the loop?" Brain Informatics (2016) vol. 3, pp. 119-131.
Holzinger, A "Beyond Data Mining: Integrative Machine Learning for Health Informatics" draft editorial paper (Apr. 2016); URL:https://online.tugraz.at/tug_online/voe_main2.getVollText?pDocumentNr=1347744&pCurrPk=89271.
Mandel, J. C et al. : SMART on FHIR: a standards-based, interoperable apps platform for electronic health records J Am Med Inform Assoc. 2016;23(5):899-908.
Trivedi, Gaurav et al. An Interactive Tool for Natural Language Processing on Clinical Text, arXiv:1707.01890 [cs.HC] Jul. 7, 2017.
Duchi, John et al. "Efficient Online and Batch Learning Using Forward Backward Splitting" Journal of Machine earning Research 10 (2009), pp. 2899-2934.
The International Search Report with Written Opinion for PCT/US2017/054213 dated Dec. 11, 2017, pp. 1-20.
Hidasi et al., "Shift Tree: An Interpretable Model-Based Approach for Time Series Classification", pp. 48-64, 2011.
Yu et al., "Integrating Relevance Feedback in Boosting for Content-Based Image Retrieval", 4 pages.
Che et al., "Interpretable Deep Models for ICU Outcome Prediction", 10 pages.
"Information Gain in Decision Trees," Wikipedia, the Free Encyclopedia. https://en.wikipedia.org/w/index.php?title=Information_gain_(decision_tree)&oldid=902831181. Jun. 21, 2019.
"Loss Functions for Classification," Wikipedia, the Free Encyclopedia. https://en.wikipedia.org/w/index.php?title=Loss_functions_for_classification&oldid=928523912. Nov. 29, 2019.

\* cited by examiner

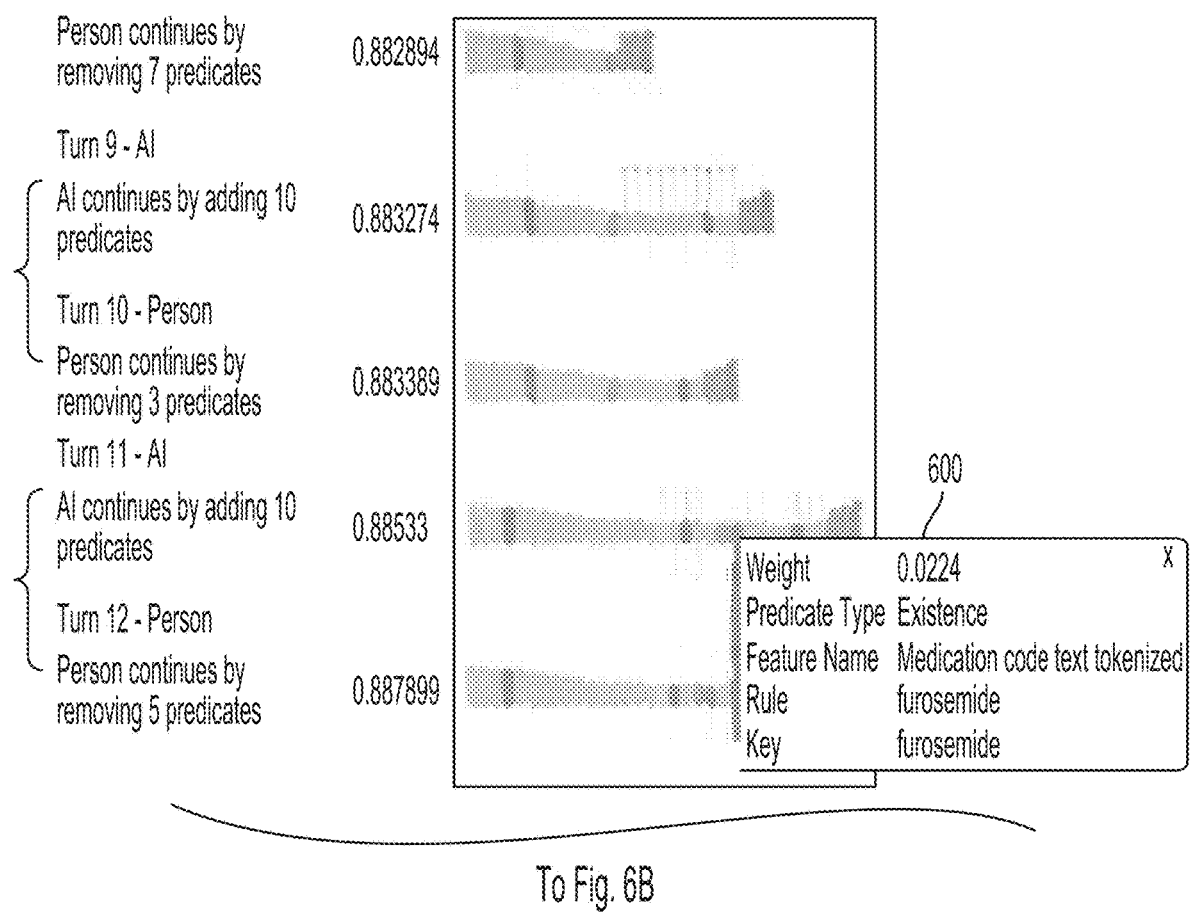

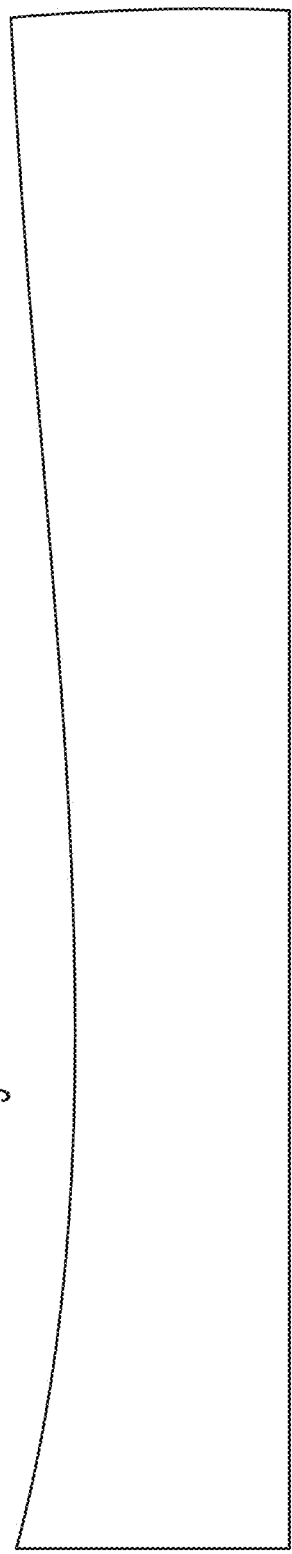
Fig. 8C
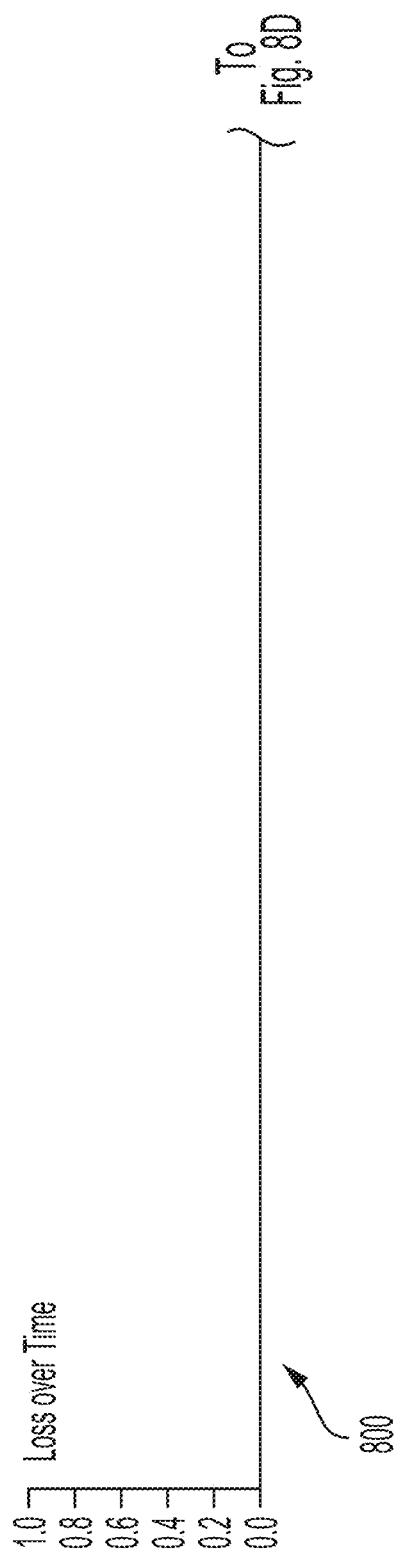

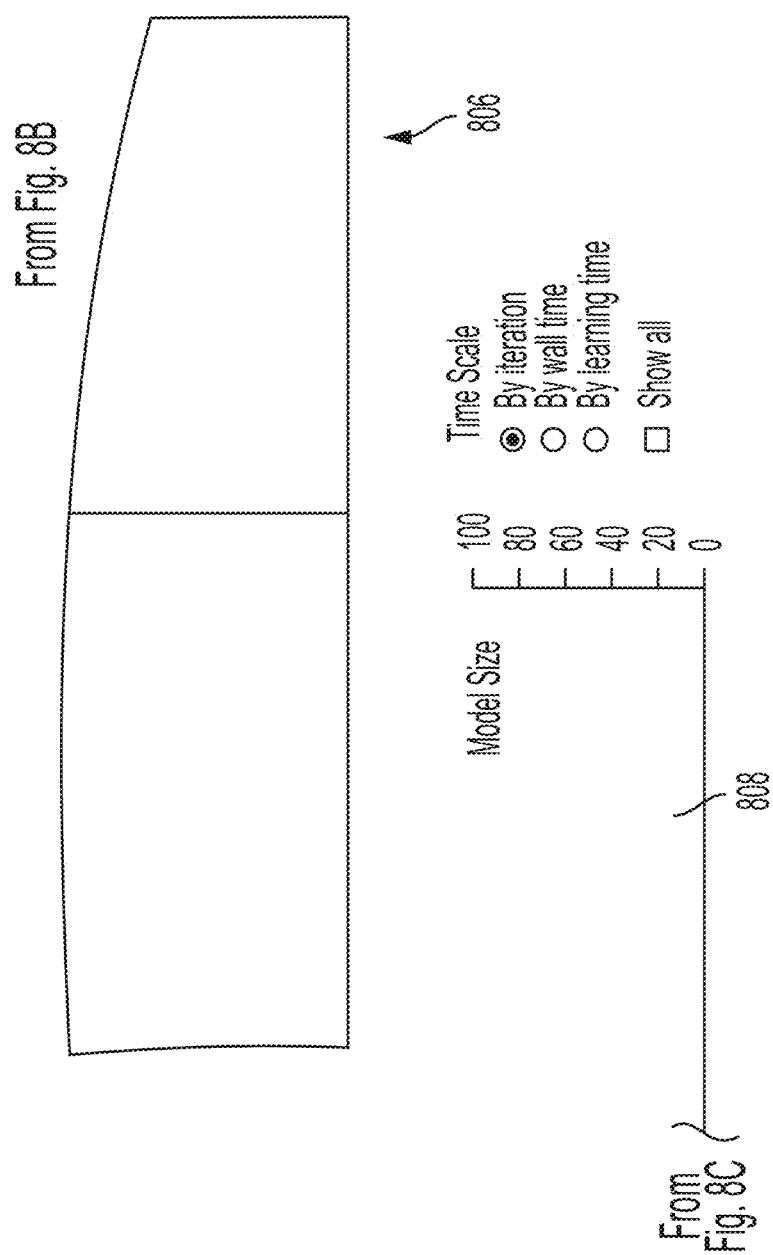

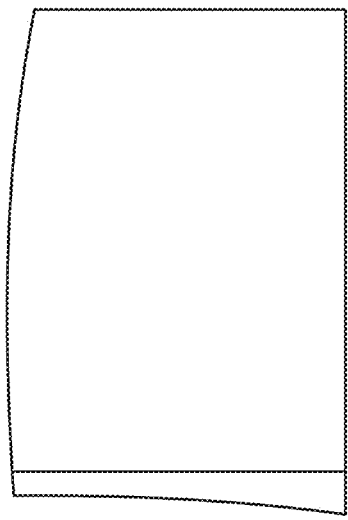

HUMAN-IN-THE-LOOP INTERACTIVE MODEL TRAINING

CROSS-REFERENCE TO RELATED APPLICATION

The present application is a national stage entry of PCT/US2017/054213 filed Sep. 29, 2017 and U.S. Provisional Patent Application 62/552,088 filed Aug. 20, 2017, the contents of which are hereby incorporated by reference.

PRIORITY

This application claims priority benefits of U.S. Provisional Application Ser. No. 62/552,088 filed Aug. 30, 2017.

BACKGROUND

This disclosure relates to the field of machine learning, and more particularly to a method of training a predictive model from underlying data.

Machine learning models, for example neural network models used in the health sciences to make predictions or establish a predictive test, tend to suffer from a problem that they are difficult to understand by end-users, such as physicians or medical researchers. The lack of understanding of how the models work leads to a lack of trust in the models. In other words, the models are not "interpretable", and are often thought of as some unknowable "black box." As machine learning models become more widely adopted to aid experts like judges and doctors to make consequential decisions, there is significant interest to ensure that such systems are more than simply accurate, they must be understandable and instill trust, a collection of traits generally referred to as "interpretable." Z. Lipton, *The Mythos of Model Intepretability*, arXiv:1606.03490 [cs.LG] (June 2016).

Interpretability has no universally agreed upon technical definition in the machine learning community, but some have proposed the following properties:

- Complexity or model size. A model that can be understood by a human in its entirety, like a sparse linear model. A variant of this is if a human could perform inference in a reasonable amount of time. This has also been called simulatability.
- Understandable. A clear relationship between how an input is considered by the model, like a node in a decision tree. This has also been called decomposability.
- Training Transparency. The method of the training, like convex optimization, has well understood properties, like those used to train linear models.
- After-the-fact end-user interpretability. That is, the model allows for an after the fact explanation of a prediction, like a saliency map, or examples of cases with similar predictions.

This disclosure presents a solution to this problem of generating interpretable models. In this regard, we describe a method of generating a predictive model that is interpretable by end-users. While the disclosure provides an example of a method of training a predictive model in the context of electronic health records, it is offered by way of example and not limitation as the method could be used in other situations where there is a desire to generate more understandable or interpretable predictive models for other types of end-users.

SUMMARY

This disclosure relates to a computer-implemented method of training a predictive model which is interpretable to end-users and inherently more understandable and hence trustworthy than other types of models, such as deep neural networks. There are several aspects which contribute this goal, including representation of "knowledge" in the model in a human-understandable form and the use of input from human operator or expert in the middle of model training. In the illustrated embodiment, knowledge in the model is in the form of human-understandable predicates. The model consists of a set of predicates and weights. The input from the human in the model training allows for the deselection of proposed predicates for the model which are deemed by the human to be not trustworthy or otherwise undesirable in the model. Accordingly, the whole model is understandable and modifiable by a human. The model also has very desirable expressiveness due to a flexible design of the predicate types.

In one embodiment, the model is built up gradually over many iterations, a technique known as boosting. The method makes use of data having a multitude of features (e.g., unstructured data such as words in text notes, medications, lab results, vital signs, previous hospitalizations, etc.). Every instance of each feature is associated with a real value (such as a vital sign or a word in a note) and a time component. The time component could be an index in a time sequence, or a time in the past relative to a current time when a prediction is generated by the model, such as some number of days, months or minutes in the past. In one embodiment, the data is structured in a tuple format of the type $\{X, x_i, t_i\}$ where X is the name of feature, $x_i$ is a real value of the feature and $t_i$ is a time component for the real value $x_i$.

The method includes a step of defining a multitude of "predicates." The predicates are binary functions operating on sequences of the tuples and return a result of 0 or 1. Predicates could also be binary functions of logical combinations of sequences of tuples, such as Predicate 1 OR Predicate 2; or Predicate 1 OR Predicate 2 where Predicate 2=Predicate 2a AND Predicate 2B). As another example, a predicate could be combination of two Exists predicates for medications vancomycin AND zosyn over some time period. The predicates can be grouped into types, such as "relatively human understandable" predicates such as Exists or Counts type predicates, and relatively less human understandable predicates. An example of an Exists predicate for feature X is "did the token/feature X exist in the electronic health record for a patient at any time?" If so, a 1 is returned and if not a 0 is returned. An example of a Counts predicate is "does the number of counts of feature X over all time in the electronic health record for a patient exceed some value C?" If so a 1 is returned, otherwise a 0 is returned. In a complex data set such as unstructured electronic health records over a large number of patients, the number of possible predicates is extremely large, potentially in the millions. However, the predicates can be designed or structured in a human understandable way. That is, the definition of the predicates can be specified by an expert (e.g., end-user) so that they are conceptually related and relevant to predictions that may be made by the model.

The method includes step of iteratively training a boosting model. The boosting model can be seeded or initialized by a bias term such a 1. The iterative training method includes the following:

1) generating a number of new predicates selected at random (in one possibility these predicates are human understandable predicates only, but this is not essential; additionally it may be possible to automatically exclude predicates that a human would delete as untrustworthy or irrelevant anyway). In one embodiment 5,000 predicates are selected at random.

2) scoring all the new random predicates by weighted information gain with respect to a class label associated with a prediction of the boosting model (e.g., the diagnostic billing code at discharge, inpatient mortality, etc.).

3) selecting a number, e.g., 10, of the new random predicates with the highest weighted information gain and adding them to the boosting model.

4) computing weights for all the predicates in the boosting model; and 5) removing one or more of the selected new predicates with the highest information gain from the boosting model in response to input from an operator or human-in-the-loop (e.g., a human expert views the predicates and removes those that are deemed to be less trustworthy, not understandable, irrelevant, or otherwise).

Steps 1, 2, 3, 4 and 5 are repeated iteratively, for example 10 or 20 times, gradually building up a boosting model. The use of a human-in-the-loop enhances the interpretability and reduces the complexity of the model by removing predicates that are not trustworthy, irrelevant, add unnecessary complexity, etc. This iterative process generates a final iteratively trained boosting model.

In one embodiment, after the final iteratively trained boosting model is generated it is evaluated, e.g., for accuracy or performance, indicia of interpretability, such as trustworthiness, complexity, human understandability, post-hoc explainability, etc.

The disclosure includes several methods for visualizing the model in the evaluation step. These can include, among others, i) displaying the iterative process of generating the boosting model by addition of predicates in each boosting round, (ii) displaying the grouping of the predicates in the final iteratively trained boosting model, e.g., by subject matter or related concepts, (iii) visualizing predicates, to make them more human understandable, as well as (iv) user interface tools for presenting proposed predicates with the highest weighted information gain and providing an expert user to deselect one or more of the proposed new predicates.

In another aspect, a computer-implemented method of training a predictive model from electronic health record data for a multitude of patients is disclosed. The data includes a multitude of features, each feature associated with real values and a time component, wherein the data is in a tuple format of the type $\{X, x_i, t_i\}$ where X is the name of feature, $x_i$ is a real value of the feature and $t_i$ is a time component for the real value $x_i$. The method includes implementing the following instructions or steps in a processor of the computer:

a) defining a multitude of predicates as binary functions operating on sequences of the tuples or logical operations on the sequences of the tuples;

b) dividing the multitude of predicates into groups based on understandability, namely a first group of relatively more human understandable predicates and a second group of relatively less human understandable predicates; and c) iteratively training a boosting model by performing the following:

1) generating a number of new random predicates from the first group of predicates;

2) scoring all the new random predicates by weighted information gain with respect to a class label associated with a prediction of the boosting model;

3) selecting a number of the new random predicates with the highest weighted information gain and adding them to the boosting model;

4) computing weights for all the predicates in the boosting model;

5) removing one or more of the selected new predicates with the highest information gain from the boosting model in response to input from an operator; and 6) repeating the performance of steps 1, 2, 3, 4 and 5 a plurality of times and thereby generating a final iteratively trained boosting model.

In still another aspect, we have disclosed an improved computing platform, e.g., general purpose computer, implementing a machine learning model. The improvement takes the form of the machine learning model being an iteratively trained boosted model built from predicates defined as binary functions operating on sequences of features having both a real value and time component. The predicates are defined with operator input the selection of predicates for inclusion in the iteratively trained boosted model are subject to review and selection or deselection by an operator during iterative training of the boosting model.

In one embodiment the features are features in electronic health records. Other types of training data sets could be used and the use of electronic health records is offered by way of example and not limitation.

In still another aspect, a workstation is disclosed for providing operator input into iteratively training a boosting model. The workstation includes an interface displaying predicates selected as having a weighted information gain for making a prediction of the boosting model, and the interface providing a tool for selection or deselection of one or more of the predicates in iteratively training the boosting model.

It will be noted that in the broadest sense, the methods of this disclosure can be used for "features" in training data where the term "features" is used in its traditional sense in machine learning as individual atomic elements in the training data which are used to build classifiers, for example individual words in the notes of a medical record, laboratory test results, etc. In the following description we describe features in the form of binary functions (predicates) which offer more complex ways of determining whether particular elements are present in the training data, taking into account time information associated with the elements. More generally, the methodology may make use of a test (or query) in the form of a function applicable to any member of the training data to detect the presence of one or more of the features in that member of the training data.

Accordingly, in one further aspect a computer-implemented method of generating a predictive model from training data is described, the predictive model being for predicting a label based on input data which, for each of a plurality of features X, indicates a value x of the feature at each of a plurality of times, and the training data comprising a plurality of samples, each sample indicating the value of one or more of the features at each of one of more times and a corresponding label. The method comprises implementing the following steps as instructions with a processor:

defining a set of predicates, each predicate being a function which generates an output when applied to time sequences of the features or logical combinations of the time sequences of the features;

generating a boosting model, the boosting model receiving as input the respective outputs of each of the set of predicates when applied to the samples of the training data; and performing a plurality of times the sequence of steps of:
(i) automatically generating a plurality of additional predicates;
(ii) adding the plurality of additional predicates to predicates already in the boosting model to form an updated set of predicates;
(iii) displaying a plurality of the updated set of predicates; and
(iv) receiving data input rejecting one or more of the updated set of predicates; and
(v) removing the rejected one or more predicates from the updated set of predicates.

BRIEF DESCRIPTION OF THE DRAWINGS

FIG. 6A and FIG. 6B are a further illustration of multiple iterations of building up of the boosting model and detailed information for one of the predicates popping up when the operator hovers over the predicate with a mouse.

FIG. 8A, FIG. 8B, FIG. 8C, and FIG. 8D (which may be referred to collectively as FIG. 8) are a screen shot of one possible form of a user interface of a computer which is used the operator or human in the loop when executing the method of FIG. 1.

FIG. 9A, FIG. 9B, FIG. 9C, and FIG. 9D (which may be referred to collectively as FIG. 9) are a screen shot of the user interface of FIG. 8 when the user has navigated to predicate selection/deselection tools during model training.

DETAILED DESCRIPTION

Figure 1:
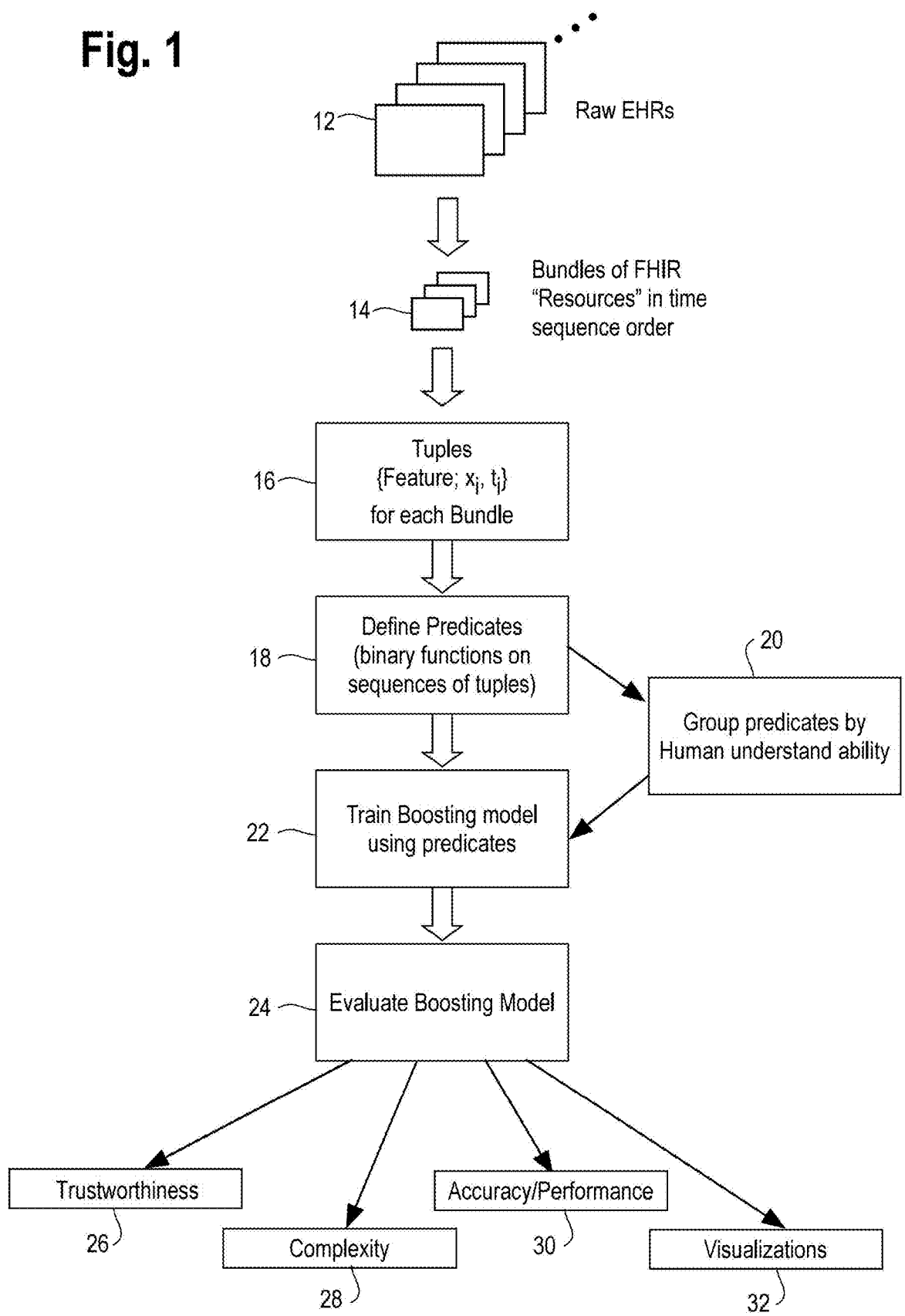
FIG. 1 is a flow-chart showing a method in accordance with this disclosure, including pre-processing, model training and evaluation steps.

This disclosure relates to a computer-implemented method of training a predictive model which is interpretable to end-users and inherently understandable and hence trustworthy. There are several aspects which contribute this goal, including representation of "knowledge" in the model in a human-understandable form and the use of input from human operator input in the middle of model training.

This document will explain how the method works in the context of a particular problem domain, but as noted above the method can be used more generally to other types of problems.

In the following discussion, the input to the model is an electronic health record (EHR) data set which is the set of medical information collected by a health system or hospital about patients, including time-stamped structured information (e.g. all medications and dosages given to patients, laboratory values, diagnoses, vital signs, procedures, etc.) and unstructured data (e.g. clinical notes). Recent rapid adoption of EHRs in the United States makes modeling on this data particular important to improve care delivery.

A patient quickly accumulates hundreds of thousands of data-points, and in clinical practice, this information cannot even be visualized in a single EHR screen. This is particularly the case in the context of high-dimensional inputs with correlated features, as is the case in personalized medicine.

In the present disclosure we describe by way of example the generation of models to make two predictions:

1. Diagnosis: Predict the primary billing diagnosis of a patient. These predictions may save the physician time looking up codes, whose accuracy can promote better secondary use of the data by health systems and researchers.

2. In-Patient Mortality: Predict whether a patient is going to die during their hospital stay; i.e., mortality of a patient. The predictions of the model can be used to guide a doctor to intensify monitoring and checkups or discuss prognosis with patients in case of a (unexpectedly) high predicted risk of mortality.

In both cases, in order to make use of the predictions the doctor needs to understand why a prediction is what it is; in other words the model needs to be interpretable.

We will now construct a toy example of two models that are equivalent when measuring their accuracy, complexity, decomposability, training transparency and end-user interpretability. However, their intuitive interpretability varies significantly.

Example 1: Model A only counts the number of breakfasts the patient had in the hospital documented by a nurse which is part of the EHR. There is a positive correlation between this features and mortality. Model B instead uses on the number of days stayed at the hospital. Both models use only a single (derived) feature, may have the same accuracy, were trained the same way and can be used to explain predictions. But a clinician finds it Model B easier to interpret.

This example motivates the addition of another property of interpretability that we call "feature-trustworthiness." Like interpretability, it is a notion difficult to measure. We offer the following definition: an input feature is "trustworthy" if it is easy to understand by itself and end-users of the model believe that the feature is directly or causally related to the predicted outcome. A model is trustworthy if the features used for explaining the model's predictions are trustworthy.

Previously, a handful of features where hand-crafted and chosen with trustworthiness in mind and models were built with these features. This method incorporates domain expert's knowledge, but is not data driven. But with the approach of scalable machine-learning better results were achieved with models that operate on all the features and automate the feature selection process. This method is at the opposite end as it is data-driven but no domain knowledge is required and the results are not interpretable. Our method can be considered as a hybrid of data-driven and domain expert guided machine learning that achieves state-of-the-art results.

A dimension of model interpretability that is underexplored in the literature is dealing with data that may not be immediately interpretable. For example, an electronic health record contains time series data of structured and unstructured data that requires domain expertise to nominally understand. The pre-processing, feature engineering, and data-augmentation to transform the raw data into features for an algorithm are necessary for end-users to understand how raw data was entered into the algorithm; the understandability of these steps are what we call "pre-processing interpretability."

There has been less research about the interaction of these different components of interpretability. In this document we describe a new machine learning model that promotes multiple aspects of interpretability, and report results on classifying diagnoses and predicting in-patient mortality using electronic medical records.

Figure 2:
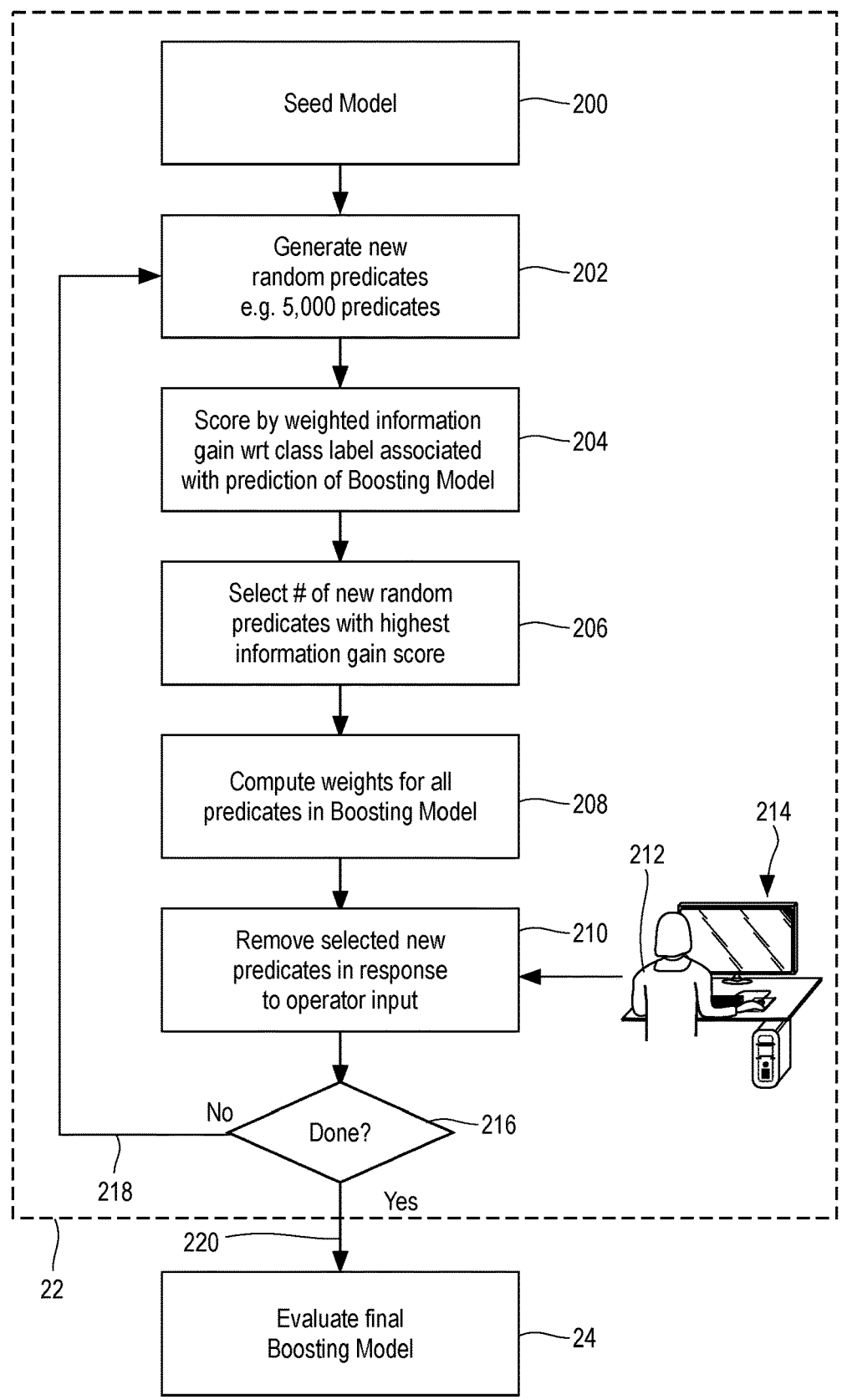
FIG. 2 is more detailed flow chart of the training step of FIG. 1.

We developed a novel machine learning method which we have called Space-Time Aware Boosting LEarner (STABLE), which is shown in FIGS. 1 and 2. By design, it extracts binary predicates directly from raw data to provide maximal pre-processing interpretability and understandable decision rules. We also trained using a standard procedure (a variant of generalized additive model) to maximize training transparency. We demonstrate that the model can achieve state-of-the-art performance on tasks on a medical dataset.

Our data set for model generation was the MIMIC-III dataset which contains de-identified health record data on critical care patients at Beth Israel Deaconess Medical Center in Boston, Massachusetts between 2002 and 2012. The data set is described in A. E. Johnson et al., *MIMIC-III, a freely accessible critical care database*, J. Sci. Data, 2016.

The EHR data looks like a sequence of events with associated time stamps. For example, a medical record might contain historical values including vital measurements such as blood pressure, weight and heart rate. Lab values over time are also present at various time scales from daily to weekly to once every few years. There are also medical notes associated at particular times. Hence the model architecture for such data is not a straightforward choice of the standard feature and label as the features here happen at a particular time.

Referring now to FIG. 1, this document describes a method 10 of generating and training a predictive model from a dataset 12. In this example, the dataset 12 is the MIMIC-III electronic heath record data set but as noted above it could be other types. It is possible that the dataset could consist of electronic health records acquired from multiple institutions which use different underlying data formats for storing electronic health records, in which case there is an optional step 14 of converting them into a standardized format, such as the Fast Health Interoperability Resources (FHIR) format, see Mandel J C, et al., *SMART on FHIR: a standards-based, interoperable apps platform for electronic health records*. J Am Med Inform Assoc. 2016; 23(5):899-908, in which case the electronic health records are converted into FHIR resources and ordered, per patient, into a time sequence or chronological order. Further details on step 14 are described in the U.S. provisional patent application Ser. No. 62/538,112 filed Jul. 28, 2017, the content of which is incorporated by reference herein.

Methodology

The data in the data set 12 contains a multitude of features, potentially hundreds of thousands or more. In the example of electronic health records, the features could be specific words or phrases in unstructured clinical notes (text) created by a physician or nurse. The features could be specific laboratory values, vital signs, diagnosis, medical encounters, medications prescribed, symptoms, and so on. Each feature is associated with real values and a time component. At step 16, we format the data in a tuple format of the type $\{X, x_i, t_i\}$ where X is the name of feature, $x_i$ is a real value of the feature (e.g., the word or phrase, the medication, the symptom, etc.) and $t_i$ is a time component for the real value $x_i$. The time component could be an index (e.g., an index indicating the place of the real value in a sequence of events over time), or the time elapsed since the real value occurred and the time when the model is generated or makes a prediction. The generation of the tuples at step 16 is performed for every electronic health record for every patient in the data set. Examples of tuples are {"note: sepsis", 1, 1000 seconds} and {"heart_rate_beats_per_minute", 120, 1 day}.

At step 18, in order to deal with the time series nature of the data, via software instructions we binarize all features as predicates and so real valued features might be represented by a space-time predicate such as heart_rate>120 beats per minute within the last hour. The term "predicate" in this document is defined as a binary function which operates on a sequence of one or more of the tuples of step 16, or binary function operating on logical combinations of sequences of the tuples. All predicates are functions that return 1 if true, 0 otherwise. As an example, a predicate Exists "heart_rate_beats_per_minute" in [{"heart_rate_beats_per_minute", 120, 1 week}] returns 1 because there is a tuple having {"heart "heart_rate_beats_per_minute", 120, 1 day} in the entire sequence of heart_rate_beats_per_minute tuples over the sequence of the last week. Predicates could also be binary functions of logical combinations of on sequences of tuples, such as Exists Predicate 1 OR Predicate 2; or Exists Predicate 1 OR Predicate 2 where Predicate 2=Predicate 2a AND Predicate 2B). As another example, a predicate could be a combination of two Exists predicates for medications vancomycin AND zosyn over some time period.

At step 20, there is the optional step of grouping the predicates into two groups based on human understandability (i.e., understandable to an expert in the field). Examples of predicates in Group 1, which are the maximally human understandable predicates, are:

Exists: X—did the token/feature X exist at any point in a patient's timeline. Here X can be a word in a note, or the name of a lab or a procedure code among other things.

Counts: #X>C. Did the number of existences of the token/feature X over all time exceed C. More generally, a Counts predicate returns a result of 0 or 1 depending on the number of counts of a feature in the electronic health record data for a given patient relative to a numeric parameter C.

Depending on the type of prediction made by the model, other types of human understandable predicates could be selected as belonging to Group 1. Additionally, human understandable predicates could be generated or defined during model training by an operator or expert.

The predicates in Group 2, which are less human-understandable, can be for example:

Any $x_{(i)}$>V at $t_{(i)}$<T. Did the value of $x_{(i)}$ exceed V at time less than T in the past (or alternatively X<=V).

Max/Min/Avg_i $x_{(i)}$>V. Did the maximum or minimum or average of X>V (or alternatively X<=V) over all time.

Hawkes process. Did the sum of exponential time decayed impulses when $x(_i)>V$ exceed some activation A over some time window T? Activation=sum$_i$ I($x(_i)$>V)*exp(-t$(_i)$/T)

Decision List predicates where any two conjunctions of the above predicates are used.

True—always returns 1. This is the first predicate (seed) in the boosting model and acts as the bias term. It is initialized to the log odds ratio of the positive class in the first batch.

Referring again to FIG. 1, at step 22 we proceed to train a boosting model using the predicates defined at step 18 (and optionally only using the human understandable predicates grouped as Group 1 in step 20). Step 22 is an iterative process of gradually building up a boosting model using input from an expert as will be explained in conjunction with FIG. 2.

In order to overcome the problem of difficulty in understanding or interpreting deep neural networks, we focused on creating a boosting model that could generate parsimonious (less complex) and human-understandable rules to make them interpretable and facilitate a natural human evaluation of them. Boosting algorithms generally combine a series of weak learners that are iteratively added if they increment performance. We use input from a human in the loop during training to selectively remove or deselect predicates which are candidates for inclusion in the boosting model. After multiple iterations of selection of predicates and removal or deselection of some of them, we arrive at a final trained boosting model, which is defined as a set of predicates and associated weights.

At step 24, we then proceed to evaluate the finally trained boosting model. As shown in FIG. 1, this evaluation process can have several components, such as evaluation of trustworthiness 26 (usually using input from an expert or group of experts), complexity 28 (based on the number of predicates remaining in the final boosting model), accuracy and performance 30, e.g., on a separate test set or a validation set or against other models; and using visualization techniques 32. In the visualization step 32 properties of the model are displayed for an operator, allowing them to inspect and evaluate the building up of the boosting model, the predicates, their weights and performance metrics. Examples of the visualizations are shown in FIGS. 3-6 and will be explained subsequently. A user interface for interactive model training will be described in conjunction with FIGS. 8 and 9 later.

Referring now to FIG. 2, the training process 22 of FIG. 1 will be described in greater detail. At step 200 a boosting is initialized or seeded, e.g., with a bias term such as 1.

At step 202, a large number of new random predicates are generated or selected. For example, 5,000 new random predicates are generated. Since the number of potential predicates can be very large, as they are the cross product of the number of tokens/features, feature values and different times, we do not generate all possible predicates per round. The actual instances of each of the rules, including the selection of variables, value thresholds and time-thresholds were generated as follows. First, pick a random patient (alternating between those with a positive or negative label as for some coding tasks the positive very rare), a random variable X, and a random time T in the patient's timeline. Time is chosen by index since events are not uniformly spaced. V is the corresponding value of X at time T and C is the counts of times X occurs in the patient's timeline. Thus, if for a picked patient, if for feature X they had M tuples, pick j uniformly from [0, M−1] to locate the tuple {X, x$(_j)$, t$(_j)$} then T=t$(_j)$ and V=x$(_j)$.

Then, generate all possible predicate types using these values. Alternatively, we could restrict the model to use only the predicate type of Group 1, to gain interpretability in the final model. Note that here it is possible to design the selection of predicates which are used to generate the model by human input so as to increase the interpretability and trustworthiness of the model.

At step 204, we then score each of the 5,000 random predicates by weighted information gain with respect to a class label associated with a prediction of the boosting model (e.g., inpatient mortality, discharge billing code, etc.). The weights for each sample (patient EHR) come from computing the probability p of the sample given the current boosting model. The importance q is then q=|label−prediction|. This means that samples that the boosting model makes errors on are more important in the current boosting round. Using the importance q and the label of the samples, one can then compute the weighted information gain of the candidate predicates with respect to the label and the current boosting model. Alternatively, one can select predicates randomly and then perform a gradient step with L1 regularization. Another method is to sample groups of predicates and evaluate for information gain, in accordance with the techniques described in the paper of Trivedi et al., *An Interactive Tool for Natural Language Processing on Clinical Text*, arXiv: 1707.01890 [cs.HG] (July 2017).

At step 206 we select a number of the new random predicates with the highest weighted information gain on a given prediction task, such as 5, 10 or 20 of them.

At step 208 we then preform a gradient fit to compute weights for all predicates. At step 208 we using gradient descent with log loss and L1 regularization to compute the new weights for all previous and newly added predicates. We use the FOBOS algorithm to perform the fit, see the paper of Duchi and Singer, *Efficient Online and Batch Learning Using Forward Backward Splitting*, J. Mach. Learn. Res. (2009).

At step 210, we then remove selected new predicates in response to operator input. In particular, an expert such as a physician 212 operating a computer 214 views the randomly selected predicates with the highest information gain and then removes those that are deemed not trustworthy or causally unrelated to the prediction task of the model. For example, if one of the predicates was "number_of_breakfasts" and the prediction task is inpatient mortality, the operator may choose to deselect that predicate because it is not causally connected to whether the patient is at risk of inpatient mortality.

In one embodiment, we show the predicates to a human (212) in an interface on the computer 214 that allows them to delete predicates based on a loose criteria of "trustworthiness," which we defined as whether the human participant believes that the predicate strongly relates to the task at hand. In this "human-in-the-loop" we prefer to build the model in the method of FIGS. 1 and 2 using the predicates in the first Group, i.e., those predicates that have a high degree of human understandability.

Additionally, it is possible to have the user interface of the workstation include a tool, such as box for entry of text, where the operator can define a predicate during building of the boosting model. For example, at steps 206 or 210 the operator could insert a new predicate and it is added to the boosting model.

At step 216 there is a check to see if the training process complete, and normally the process loops back after the first iteration using No branch and loop 218 is taken to repeat steps 202, 204, 206, 208 and 210 multiple times, such as ten or twenty times. Each iteration through the loop 218 results in the gradually buildup of more and more predicates. Each predicate has a high weighted information gain score (from step 204), and with an inspection and possible deselection of some predicates by the human operator in step 210. Accordingly, the methodology gradually builds up an accurate, trustworthy and interpretable model. Moreover, by virtue of the design and selection of human understandable predicates, and the human inspection and possible removal of predicates that lack sufficient trustworthiness, the methodology results in a final generated boosted model that is interpretable to end-users and overcomes the problems with the prior art.

After a sufficient number of boosting rounds (loop 218) have been performed, for example the performance metrics meet expected criteria, the yes branch 220 is taken and the process proceeds to the evaluation step 24 of FIGS. 1 and 2.

As noted previously, the evaluation can take the form of human evaluation of the model for trustworthiness, complexity (did the model have a reasonable number of features), and accuracy. For measurements of accuracy one can investigate how the model performed on a test set relative to other models generated from the data, as well as the use of test metrics such as the area under a receiver operating characteristic curve (AUROC), a known performance metric in machine learning.

In order to analyze the performance of the model built in accordance with FIGS. 1 and 2, we generated several other models from the data set, including one that used the methodology of FIGS. 1 and 2 but did not use a human in the loop in step 212 and used all predicate types, including those of Group 1 and Group 2, another one that used just the simple (Group 1) predicate types, and another one that used only the Group 1 predicate types and pruned the final model to only have the same number of predicates as that resulting from the human in the loop. The performance of the various models is described in some detail below.

In one embodiment, the evaluation step 24 could consist of the following:
1. Accuracy. We used the AUROC for performance of the model on a validation set.
2. Complexity. We counted the number of predicates at the end of training.
3. Trustworthiness. For each task, we randomly picked X predicates from each of the models (inpatient mortality, diagnosis at discharge). We had a physician evaluate each predicate from a scale of 1 to 3, with 1 indicating a predicate was not related to the task at hand (e.g. an antibiotic not related to heart failure) to 3, indicating a predicate was strongly related to the task. We report the "Trust Score" or trustworthiness of a model by the averaged score of all its predicates.

Figure 3:
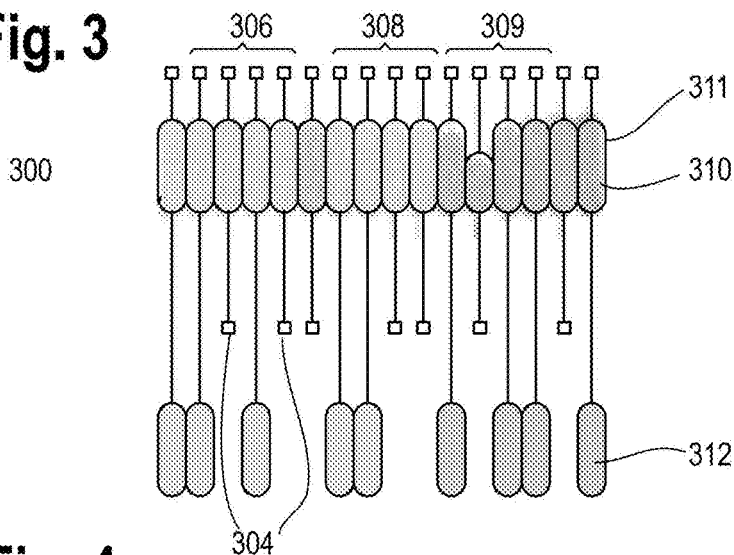
FIG. 3 is illustration of visualization of one iteration of an initial set of predicates with highest weighted information gain and the deselection of some of the predicates by an operator.

As noted previously, one of the ways of evaluation of the model generated in accordance with FIGS. 1 and 2 is by visualizations. FIG. 3 shows one example of an interactive visualization 300 for exploring human and machine participant choices during a session of model training using FIG. 1. After an iteration of the loop 218, we render the predicates as a row 310 of "lozenges" or shapes 301, each representing one predicate and its weight in the current model. The weight could be visualized by hovering over the lozenge with a mouse or it could be displayed below the lozenge (not shown in FIG. 3). The row 310 shows the first iteration of the loop 218 (FIG. 2), where the model selects and recommends 16 predicates (solid squares leading down from above). The predicates in the row 310 are grouped by subject matter, e.g., a first group 306 (e.g., words or phrases in medical notes), vital signs 308, medications 309. Of those, the human participant, a physician in this case, elected to remove 7 of those predicates from consideration. The remaining predicates are then reproduced on line 312. The removed predicates are represented by the descending lines leading to empty squares 304. The predicates are sorted by weight from highest to lowest, that is the highest weighted predicates within a group are on the left. The bias term is at the far right at 311. After each iteration, the computer (214) computes an AUROC metric which we can present as a numerical parameter and display with the visualization of the predicates.

Figure 4:
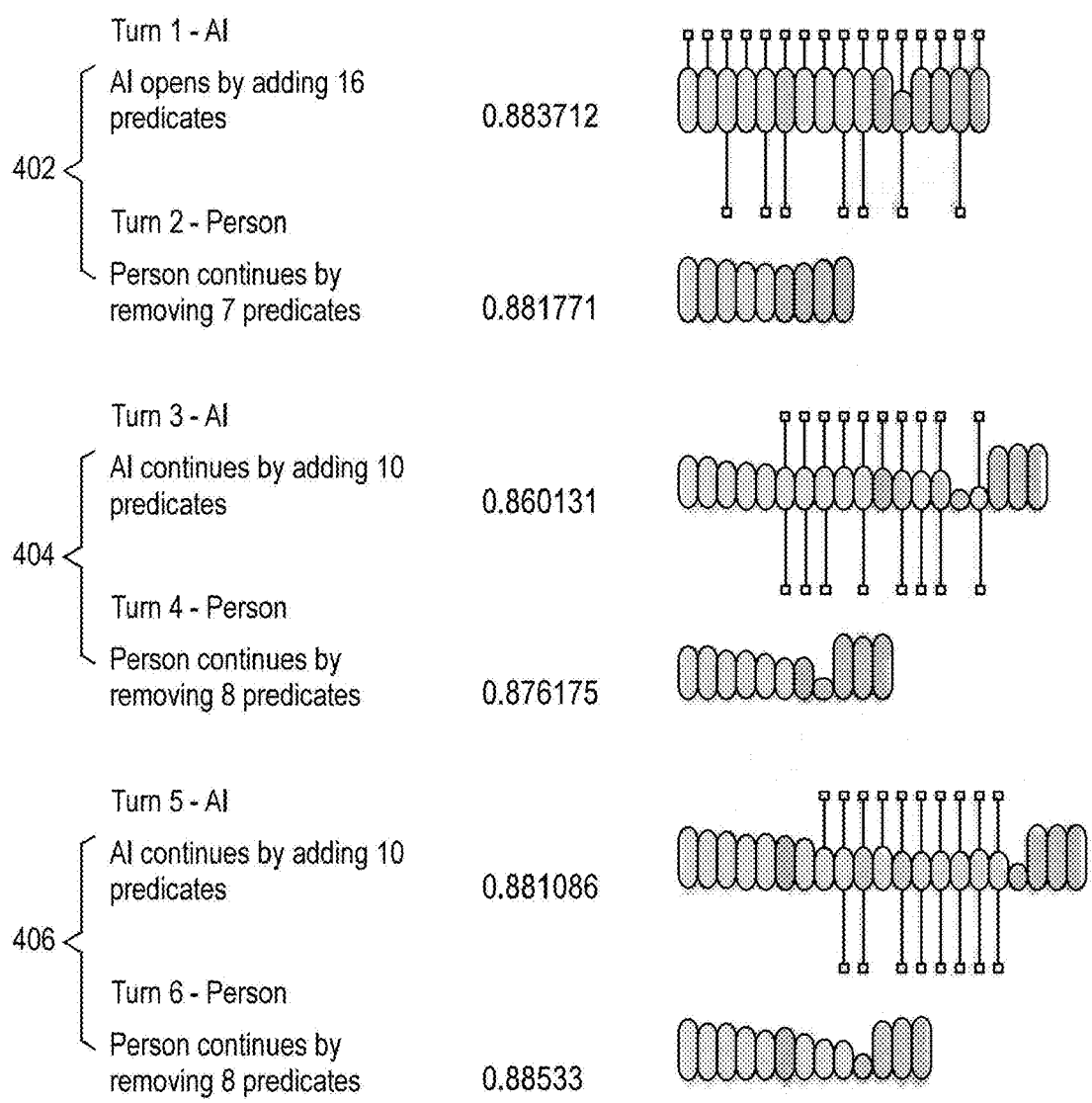
FIG. 4 is an illustration a visualization of multiple iterations of adding predicates to a boosting model and removing some of them.

In FIG. 4, the display shows a three more iterations 402, 404 and 406 of the loop 218 from the same session. In the iteration 402, "Turn 1" refers to the selection of the random predicates with highest weighted information gain and "Turn 2" represents the human in the loop removing selected predicates in that iteration of the loop. The AUROC curve calculation is shown at 408 for each step in the iterations. Note that the AUROC does not always increase each turn, but generally increases as the model is built up over successive boosting iterations.

Figure 5:
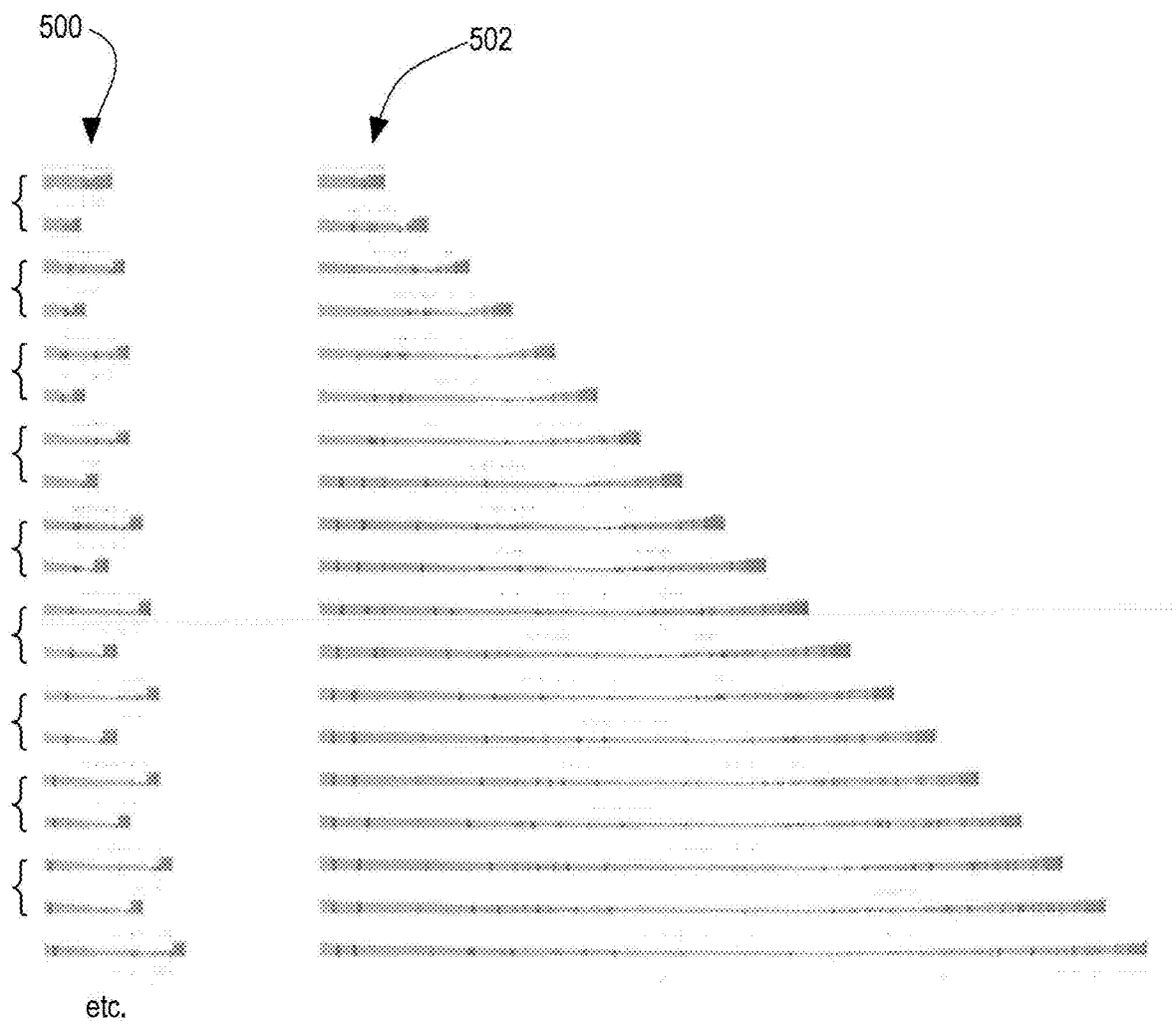
FIG. 5 is an illustration of the visualization of the buildup of the boosting model using a human in the loop over multiple iterations on the left side of the figure and the buildup of a boosting model without a human in the loop in a purely machine learning approach in the right hand side of the figure. The individual predicates are color-coded by conceptual type of predicate (i.e., the portion of the health record where the data for the predicate originated), and shown in different sizes, where size corresponds to weight in the model.

FIG. 5 shows the development of a boosting model over many iterations. In column 500, there is shown the gradual building up of the boosting model with a human in the loop, whereas the region 502 shows the gradual building up a purely machine learning boosting model with no human in the loop, with each iteration of the loop adding the 10 new random predicates with the highest weighted information gain. Note that after 9 iterations the human in the loop (physician curated) model has roughly 20 predicates in the model but the purely machine learning model has 90 different predicates (ten predicates added per round for nine rounds). If the process were to continue for another 10 rounds, the human model may end up with say 25 or 30 predicates total, whereas the purely machine learning model would have 190 predicates. In terms of complexity, the human in the loop model indicated by column 500 would be much less complex and hence more interpretable. Both models achieve an AUROC of 0.89 after the 19th iteration. However, the physician curated model contains many fewer model parameters.

Figure 6B:
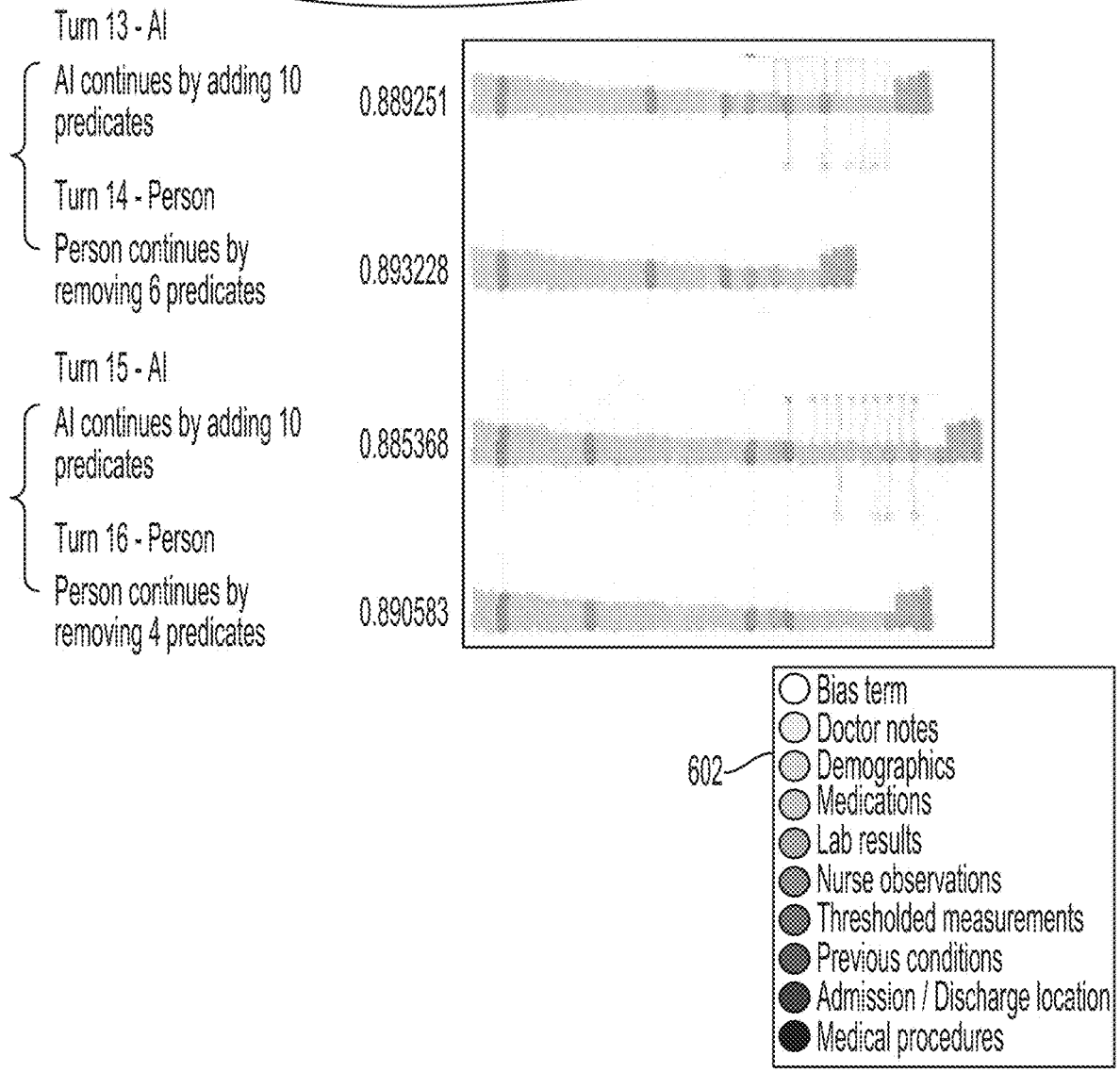

Our interactive visualization allows a user to dynamically explore the learned predicates by choosing from several sorting and coloring options. In FIG. 6 the predicates are sorted by weight magnitude, where the size of the "lozenge" is scaled in accordance with the weight, with higher weighted predicates rendered in a larger size. Additionally, the user can hover over the predicate/lozenge and a box 600 pops up which shows details of the predicate, such as its weight, its type, the feature name (token), rule, key and other attributes. Additionally the "lozenges" can be color coded by concept or type, as indicated by the color code key shown at 602.

Example Text Interface for Training

The workstation 214 can provide a text interface for the operator/expert to use during model training. This section will provide an example of a text interface for building a model for prediction of congestive heart failure as the diagnosis at discharge.

Each line represents a predicate in the model. The information at the beginning of each line is the meta-info about each predicate: its index, human decision about whether to keep it, a visual tag for human indicating whether it is a new predicate, and the predicate weight. The second part of the each line is the predicate itself. "E" means the existence of a feature, and "#" means the count of a feature with a threshold. "TRUE" simply captures the bias of the label in the data set. In the example below, the human decides to 'delete' the predicate at index 2, since the feature count's threshold is not trustworthy. This model is very simple, because this is at the very beginning of model training; later the model will become much larger and more complex. Since the model is composed of a set of predicates, it is still possible for human to inspect the whole model, e.g., by scrolling through the lines or by use of visualization techniques such as show in FIGS. 3-6. Rule #, Keep?, Weight

[0, Y, -, 0.0244] E:obsloinc:33762-6 pg/mL (Natriuretic peptide.B prohormone N-Terminal)
[1, Y, -, 0.0240] E:Composition.section.text.div.tokenized failure
[2, Y, -, 0.0237] #:Composition.section.text.div.tokenized ventricular>=11
[3, Y, -, 0.0237] E:Composition.section.text.div.tokenized congestive
[4, Y, -, 0.0232] #:Composition.section.text.div.tokenized regurgitation>=3
[5, Y, -, 0.0232] E:Observation.code.Ioinc.display.tokenized
[6, Y, -, 0.0228] #:Composition.section.text.div.tokenized exertion>=2
[7, Y, -, 0.0224] E:Composition.section.text.div.tokenized lasix
[8, Y, -, 0.0220] E:Composition.section.text.div.tokenized la
[9, Y, -, 0.0216] E:Composition.section.text.div.tokenized regurgitation
[10, Y, -, 0.0206] Context age_in_years>=60.000000 @ t<=1.000000
[11, Y, -, -0.0101] E:Context Patient.gender male
[12, Y, -, -0.0220] Context age_in_years>=40.000000 @ t<=1.000000
[13, Y, -, -0.0244] Context age_in_years>=18.000000 @ t<=1.000000
[14, Y, -, -0.0256] E:Context Patient.genderfemale
[15, Y, -, -3.3718] TRUE
New Model Test Score: 0.883712, Rules: 16
BOOST>delete 2

Figure 8A:
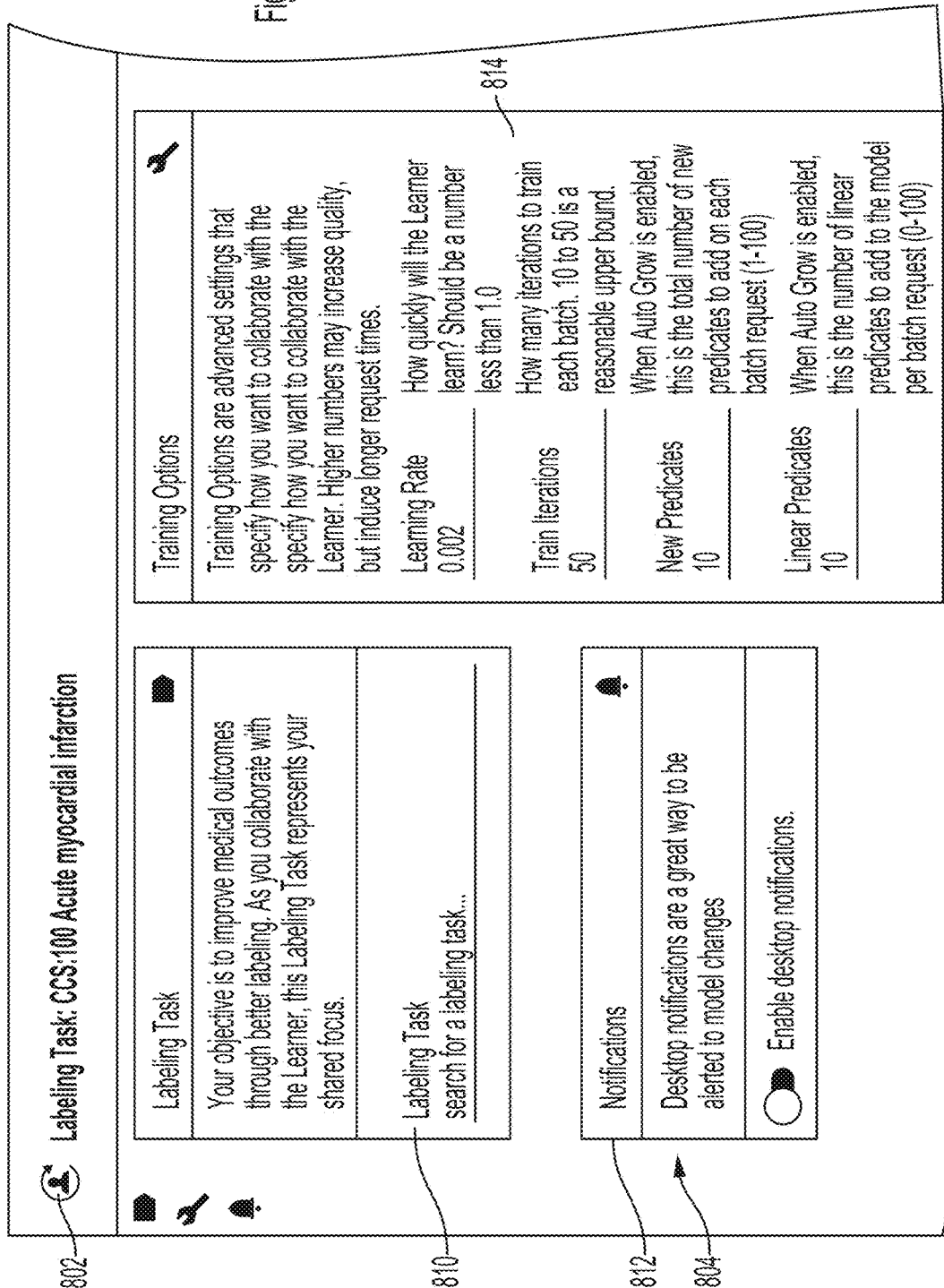
Figure 8B:
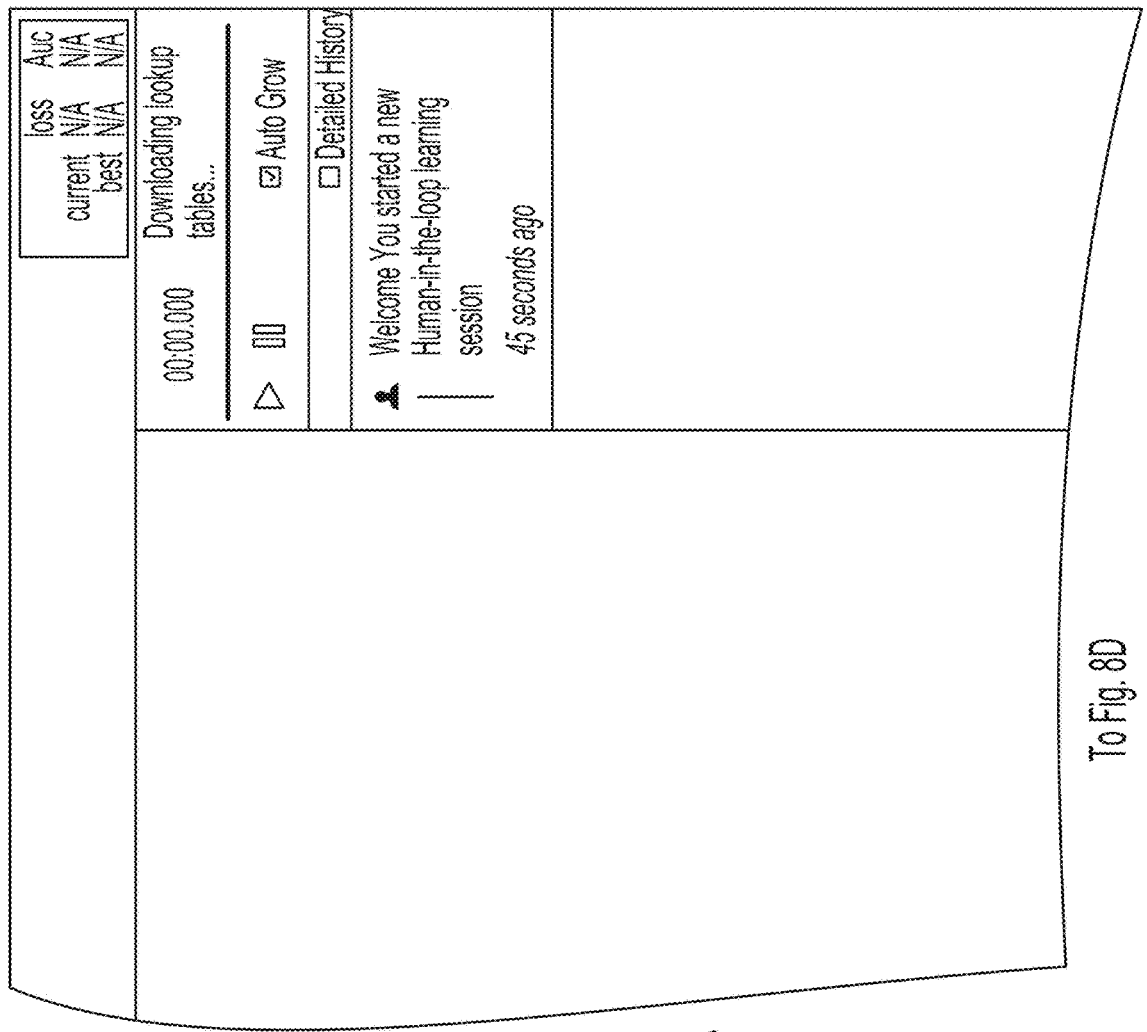
Figure 9A:
Figure 9B:
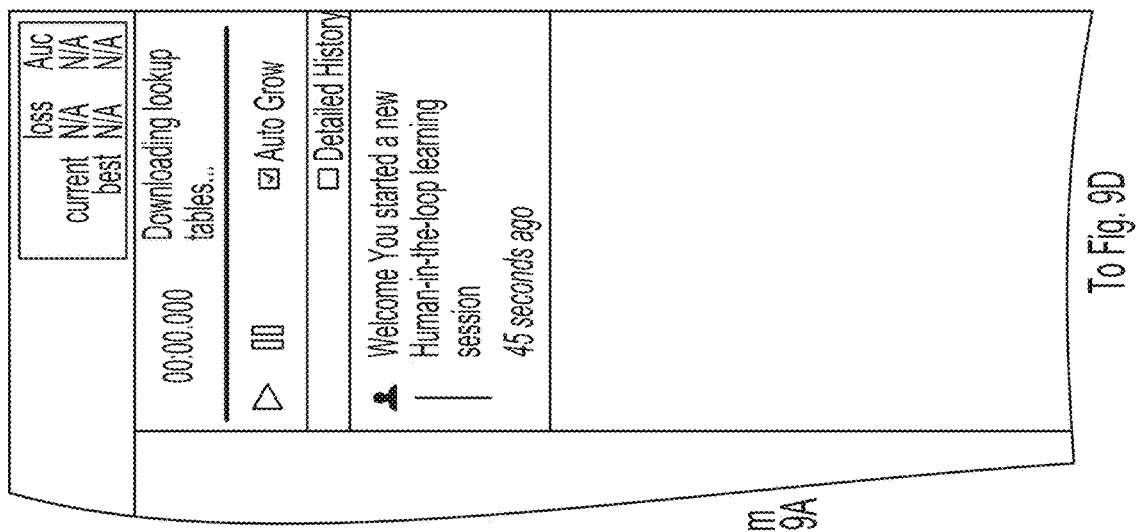
Figure 9C:
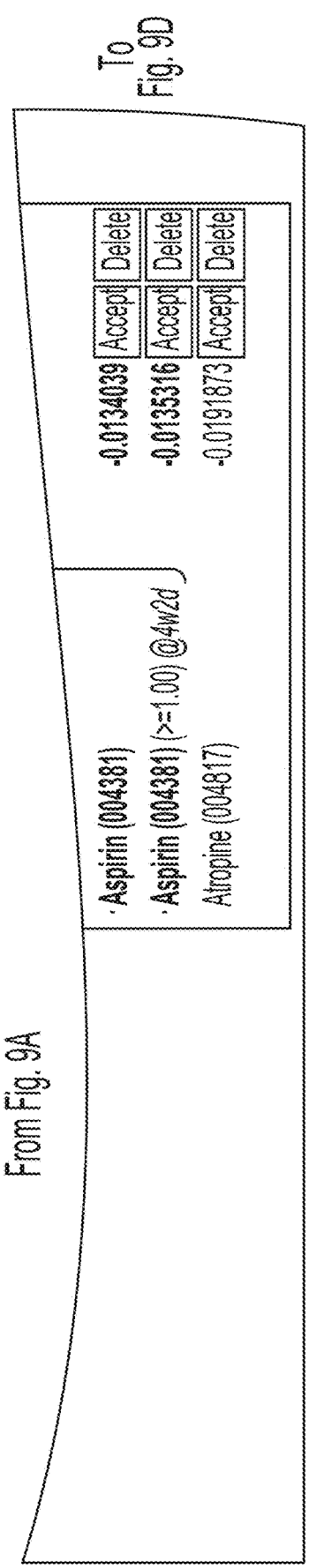
Figure 9C:
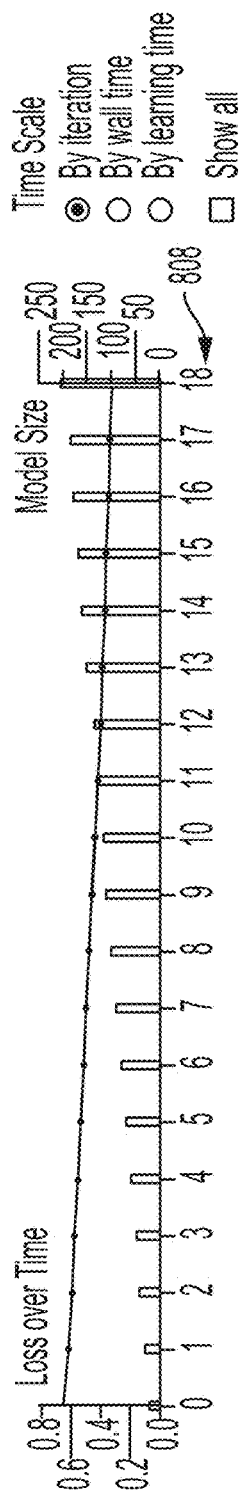

A user interface for interactive model training in accordance with FIG. 1 is shown in FIGS. 8 and 9. The model training methodology can be coded as an application executed by a general purpose computer. FIG. 8 is a screenshot of the application user interface 800 at startup. FIG. 9 shows the user interface after several rounds of interactive model training. The interface of FIGS. 8 and 9 consists of the following main areas, shown in FIG. 8:

A header bar 802 which identifies the current model labeling or prediction task (in this case prediction of acute myocardial infarction). The header bar 802 also includes some statistics shown at the right hand edge of the bar about the current session, available at a glance, such as loss and area under the curve of a receiver operator characteristics plot.

A content area 804 which provides the display of tools for modifying learner behavior and working with predicates (i.e., selecting or deselecting predicates), and showing statistics such as weight of predicates, see description of FIG. 9 below.

A control bar 806 which provides for the display of tools for requesting and saving models and a history of user actions in the current session.

A timeline 808 which summarizes the user's session with the learner by showing performance and model size metrics.

The content area 804 is a scrollable region containing "cards" (individual graphical display regions) that drive the bulk of the interaction between the user and the learner. There are two kinds or types of cards, Setting Cards and Predicate Cards. In FIG. 8, Setting Cards are shown including a labeling task card 810, a notifications card 812 and a training options card 814. The Setting Cards are available at the start of the application and appear at the top of the content area 802. The Setting Cards allow the user to modify global settings such as the learning task, tuning parameters of the learner (learning rate, batch size, etc.) initializing predicates for labeling, and toggling desktop notifications.

The Predicate Cards are shown in FIG. 9. These cards 902, 904 and 906 appear after the leaner has mined for predicates. Each Predicate Card 902, 904 and 906 organizes predicates within a category. In FIG. 9, Demographics, Doctor Notes, and Medications are the predicate cards which are shown at 902, 904 and 906, respectively, and the user can scroll down to see predicates for other categories. Newly selected predicates based on weighted information gain are shown in bold font on the display of FIG. 9 and at the top of the list of predicates within each category, as indicated at 912. Predicates which have been proposed and selected by the user in previous boosting rounds are shown in normal font below the newly proposed predicates. The display provides the tool in the form of "accept" and "delete" icons 908 and 910, respectively, by which the operator can choose to either add the proposed predicate to the boosting model or remove it. For example under the NDC subcategory of medications, the user can choose to add the predicate for medication "17714001110 . . . " by activating the "accept" icon 908 in which case this predicate will be added to the boosting model. In order to assist the user to make sense of the predicates which are listed the interface may provide for additional tools such as graphical tools, a dictionary or other which pops up when the user hovers the mouse over the predicate to explain in plain language what the predicate means, for example the plain language meaning of the medication given by the code 17714001110. The numbers immediately to the left of the "accept" and "delete" icons are the weights in the current boosting model that are assigned to the predicates which are listed.

Note in FIG. 9 the user has the option to remove predicates from the boosting model which were added in previous rounds, as indicated by the presence of the "accept" and delete" icons next to each of the predicates which are shown in the display of FIG. 9.

The number and identification of categories of predicates can of course vary, but in the present context the following categories are recognized: demographics, doctor notes, medications, lab results, nurse observations, previous conditions, admission/discharge and medical procedures. If a predicate does not fit into one of these categories it is placed in a further category called Other.

The Timeline shown at the bottom of FIG. 9 tracks the model size and its performance at the selected task over time as the boosting model is gradually built up. As the user prunes the predicate list and the learner adds more predicates, one expects and hopes to see the model size stabilize while performance metrics continue to improve (loss decreases with further iterations) without sacrificing interpretability. The illustrations of FIGS. 3-5 basically show one possible variation of the timeline shown at the bottom of FIG. 9. The timeline of FIG. 9 contains vertical bars which show the model size in terms of the number of predicates. It also contains a line chart that tracks the model's quality over time, expressed as loss. The scales for loss and model size are shown at the left and right hand edges of the timeline, respectively. Here, the term "loss" refers to logistic loss. The expression "minimizing the loss" is simply the name for the procedure for fitting the weights of the boosting model. When the loss gets close to zero it means that the model has converged and is essentially "fully cooked" and ready to use.

While the interface of FIGS. 8 and 9 illustrate one method by which tools can be provided to a human operator to build models in accordance with this disclosure of course the details of the interface can vary and the preceding description is offered by way of example and not limitation.

Results

In our work we have developed models using the procedure of FIGS. 1 and 2 and compared the results with boosting models obtained from predicates without the human-in the loop step 210 of FIG. 2.

We explored the effects of the use of predicates of type Group 2 (more complex, less human understandable) in the training of the purely machine learning model ("MM") versus the use of Group 1 (less complex, more human understandable) predicates in the human-in-the-loop model ("HM"). We found that the effect of using Group 2 predicates depends on the nature of the prediction tasks. For the tasks of predicting discharge diagnosis code, the gap between two different MM models, one with both Group 1 and Group 2 predicates (MM1) and one using just Group 1 predicates (existence and counts predicates) MM2 is rather insignificant. For example, in one discharge code task, using the AUROC metric, MM1 achieves 0.910 vs MM2's 0.896 (a gap of 0.4%). In another discharge code task, the comparison is 0.916 vs 0.914 (a gap of 0.2%). In the more complex task of mortality prediction, the gap is somewhat significant, i.e. 0.791 vs 0.814 (a gap of 2.3%). However, since one of the goals of the present inventive method is to improve on model interpretability, machine models which use the simple predicate types are preferred otherwise it is very hard for a human to understand the model. This shows the tradeoff of model quality and interpretability, but we believe it is a good tradeoff to make in the medical domain, since interpretability and trustworthiness are extremely important.

We also explored the effect of putting the human in the loop and comparing the performance of the resulting model (HM1, constructed per FIGS. 1 and 2) with two machine only models, one with Group 1 predicates (MM2) and another one which was the same as MM2 but pruned back to have the same number of predicates as the human in the loop model (MM3). We asked a domain expert (medical doctor) to guide the model's building process using the simple text interface, as described above, by deselecting predicates. We wanted to see the effect of human-in-the-loop, in terms of model quality, model size, and trustworthiness. We compare to two machine model settings: MM2 and MM3.

We have two general observations about human behavior in this process: 1) The domain expert makes decision about whether to keep or delete a predicate based mostly on trustworthiness. Under this mindset, the expert is acting on behalf of the end-users who will use this model. 2) We have a mechanism to evaluate the current model on demand, in order to help the human make decisions. However, we observe that the expert almost never relies on that in making decisions. This may explain why the HM1 model got a much higher "trust score", as shown below. Table 1 shows the quality (AUROC curve), size and trust scores for the three models in a task of classifying congestive heart failure as the diagnosis at discharge.

TABLE 1

| Task Task: Classify Congestive Heart Failure (CCS code 108) | | | |
|---|---|---|---|
| Model | HM1 | MM2 | MM3 |
| Quality | 0.904 | 0.916 | 0.917 |
| Size | 62 | 202 | 62 |
| Trust | 2.52 | 1.70 | 1.97 |

Similar quality and size results were obtained for a task of classifying Dysrhythmia as a diagnosis at discharge (CCS code 106). From model quality perspective, the human model (HM1) is very comparable with the machine models (MM2 and MM3) in the two coding tasks. In the more challenging task of predicting inpatient mortality, the HM model did worse (~5%) than MM2, and is comparable with MM3. In this task, the model was not able to suggest very interpretable predicates, and hence they are frequently deleted by human, leading to an overly small model with only 23 predicates.

From model size perspective, the human model is much smaller than the machine model (MM2). Having a smaller model allows others to inspect the model more easily; it is not strictly required but it is highly desirable, especially in the medical domain.

The most striking results is the "Trust Score" of different models. The human expert model (HM1) is rated much higher in the model's trustworthiness, which is a very desirable result. When we prune the machine model's predicate to only include the ones with highest weights (MM3), its "Trust Score" also improved (from 1.70 to 1.97), suggesting that the machine model associates higher weights for the more trustworthy predicates. Nevertheless, given the much higher "Trust Score" of the human model (HM1), its smaller model size, and comparable quality, HM1 demonstrates that our objective of obtaining an interpretable, trustworthy machine learning model has been achieved.

Further Considerations

In order to further assist the user in probing and improving the model during model training, it may be desirable to add additional features to the workstation of FIG. 1 to allow various operations by the human to be performed. For example, the user could be allowed to suggest or define predicates to the model, for example "does X exist in the notes" where X is some word or phrase relevant to the predication of the model, and use them in the next iteration of the boosting.

As another example, some more complex predicates may be initially difficult to understand even to an expert, but they may be rendered in graphical form which increases understanding by the expert and may allow them to choose them for inclusion in the model.

Additionally, many predicates may be redundant and it is preferable to select and use for model building a particular one based on its greater ability to be understood by the end-user. In order to reduce the amount of time needed to build the model it is preferable to delete or remove from the training process not only the redundant predicates but also those that the human would delete anyway, for example irrelevant ones or ones that are not human understandable.

Also, it is possible to rank the predicates such that more specific predicates have a higher priority. For example, lab test results could be preferred or ranked higher than a lab test name predicate. This can be done by using some policy rules and adjusting the weighted information scores (or the weights for the model) during the iterations of FIG. 2.

Additionally, it may be preferable to use bigrams (two words) over unigrams (one word) in predicates obtained from unstructured medical notes because bigrams provide more context and make the predicate easier to understand. The bigrams could be weighted or scored using policy rules or otherwise. Furthermore, the user interface of the workstation of FIG. 2 could show some example partial sentences or excerpts from medical notes in which these words are used.

Other preferences could be defined, either as predicates defined by the user during the iterations of FIG. 2 or by adjusting the weighted information gain for predicates. For example, humans prefer more specific notes such as "congestive heart failure" over just "heat failure" or "heart" or "failure". Longer text predicates can lead to better model performance than single words. Additionally, it may be possible to define note predicates for model training which use terms found in medical text books or dictionaries, or only use such predicates. In another example, one could also restrict the Existence predicates to tokens (words) that frequently occur in medical textbooks. In essence, during model training the process solicits the knowledge encoded in the expert's brain and transfers that knowledge into the model.

Additionally, to aid the user in deciding to select or deselect predicates, or define new predicates for use by the model, it may be useful to provide statistics to assist the user. For example, one can define "coverage" as the number of examples for which a particular predicate is true, "precision" as the number of examples with a true label for which this predicate is true divided by coverage, and "recall" as the number of examples with a true label for which this predicate is true divided by the number of examples with a true label, and a correlation between the predicate and the label.

Figure 7:
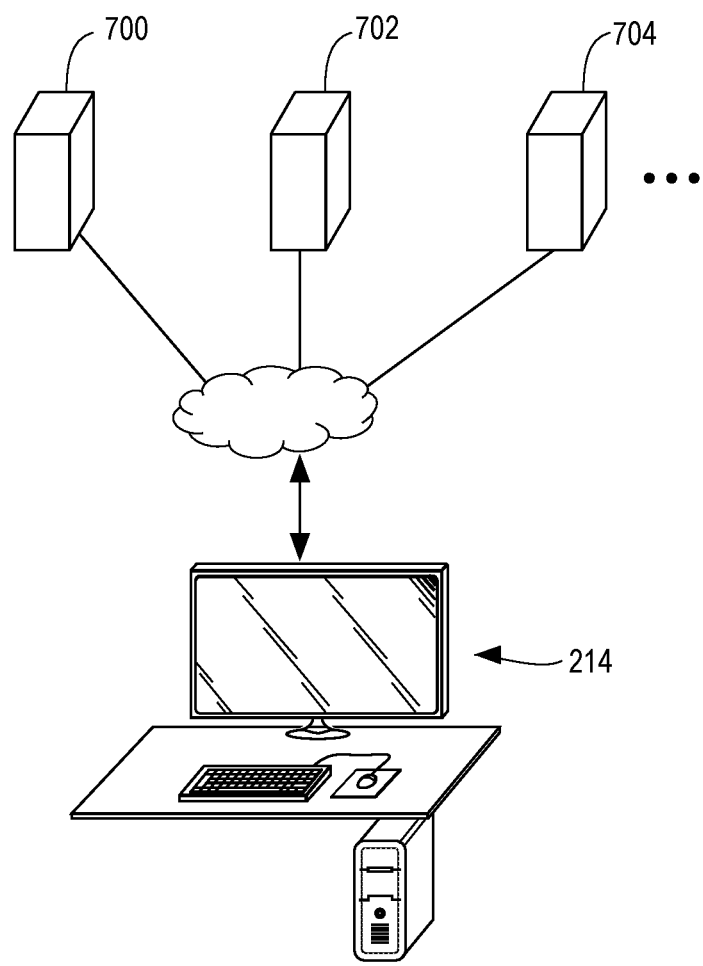
FIG. 7 is an illustration of a computer network environment in which the method may be practiced.

It is desirable to be able to build the models quickly by distributing the processing task among several servers or computing platforms during model training with a goal of reducing fatigue on the human-in-the-loop. Basically, with reference to FIG. 7, we load the entire data set (the development set of electronic patient records used to develop the model) into memory so that the model can be computed quickly. This is done by loading parts of the data set onto different servers (700, 702, 704, etc.) and at each boosting round (iteration of FIG. 2) querying a different server in round robin fashion. Each server 700, 702, 704, etc. can hold a subset of the patient electronic health records with all of the features, say 1000 patients each, and we update the model in batches of 1000 patients per round of boosting.

Another enhancement to the method is to reduce the time periods (sequence of tuples in the defined predicates) to human-friendly time periods, such as the last hour, the last day, the last week, the last month, instead of arbitrary time periods.

We claim:

1. A computer-implemented method of training a predictive model from data comprising a multitude of features, each feature associated with a real value and a time component, comprising the steps of executing the following instructions in a processor of the computer:

a) defining a multitude of predicates as binary functions operating on time sequences of the features or logical operations on the time sequences of the features;
   b) iteratively training a boosting model by performing the following:
      1) Generating a number of new random predicates as binary functions operating on at least one of (i) time sequences of the features or (ii) logical operations on the time sequences of the features;
      2) Scoring all the new random predicates by weighted information gain with respect to a class label associated with a prediction of the boosting model;
      3) Selecting, from the new random predicates, a number of the new random predicates that are the highest with respect to their weighted information gain scores and adding them to the boosting model;
      4) Computing weights for all the predicates in the boosting model;
      5) Removing one or more of the selected number of the new random predicates from the boosting model in response to input from an operator; and
      6) Repeating the performance of steps 1, 2, 3, 4 and 5 a plurality of times and thereby generating a final iteratively trained boosting model.

2. The method of claim 1, further comprising the step of c) evaluating the final iteratively trained boosting model.

3. The method of claim 2, wherein the evaluation step (c) comprises evaluating the final iteratively trained boosting model for at least one of accuracy, complexity, or trustworthiness.

4. The method of claim 1, wherein the data is in a tuple format of the type $\{X, x_i, t_i\}$ where X is the name of feature, $x_i$ is a real value of the feature and $t_i$ is a time component for the real value $x_i$, and wherein the predicates are defined as binary functions operating on at least one of (i) sequences of tuples or (ii) logical operations on sequences of the tuples.

5. The method of claim 4, wherein the sequences of tuples are defined by time periods selected from the group consisting of 1 or more days, 1 or more hours, 1 or more minutes, or 1 or more months.

6. The method of claim 1, wherein the data comprises electronic health record data for a multitude of patients.

7. The method of claim 1, wherein the method further comprises the step of dividing the predicates into groups based on understandability, namely a first group of relatively more human understandable predicates and a second group of relatively less human understandable predicates and wherein the new random predicates are selected from the first group.

8. The method of claim 7, wherein the data comprises electronic health record data for a multitude of patients, and wherein the set of predicates are represented in a manner to show the subject matter or source within the electronic health record data of the predicates.

9. The method of claim 8, wherein the predicates comprise an existence predicate returning a result of 0 or 1 depending on whether a feature exists in the electronic health record data for a given patient in the multitude of patients; and a counts predicate returning a result of 0 or 1 depending on the number of counts of a feature in the electronic health record data for a given patient in the multitude of patients relative to a numeric parameter C.

10. The method of claim 1, wherein step b) 5) further comprises the step of graphically representing the predicates currently in the boosting model and providing the operator with the ability to remove one or more of the predicates.

11. The method of claim 10, further comprising the step of graphically representing the weights computed for each of the predicates in step b) 4).

12. The method of claim 1, further comprising the step of graphically representing a set of predicates added to the boosting model after each of the iterations of step b) 6).

13. The method of claim 1, wherein step b) further comprises the step of providing the operator with the ability to define a predicate during model training.

14. The method of claim 1, wherein step b) further comprises the step of removing redundant predicates.

15. The method of claim 1, further comprising the step of ranking the predicates selected in step b) 3).

16. The method of claim 1, further comprising the step of generating statistics of predicates in the boosting model and presenting them to the operator.

17. The method of claim 1, wherein in step b) 5) the one or more predicates are removed which are not causally related to the prediction of the boosting model.

18. A computer-implemented method of training a predictive model from electronic health record data for a multitude of patients, the data comprising a multitude of features, each feature associated with real values and a time component, wherein the data is in a tuple format of the type $\{X, x_i, t_i\}$ where X is the name of feature, $x_i$ is a real value of the feature and $t_i$ is a time component for the real value $x_i$, comprising the steps of implementing the following instructions in a processor of the computer:
   a) defining a multitude of predicates as at least one of (i) binary functions operating on sequences of the tuples or (ii) logical operations on the sequences of the tuples;
   b) dividing the multitude of predicates into groups based on understandability, namely a first group of relatively more human understandable predicates and a second group of relatively less human understandable predicates;
   c) iteratively training a boosting model by performing the following:
      1) Generating a number of new random predicates from the first group of predicates as binary functions operating on at least one of (i) sequences of the tuples or (ii) logical operations on the sequences of the tuples;
      2) Scoring all the new random predicates by weighted information gain with respect to a class label associated with a prediction of the boosting model;
      3) Selecting, from the new random predicates, a number of the new random predicates that are the highest with respect to their weighted information gain scores and adding them to the boosting model;
      4) Computing weights for all the predicates in the boosting model;
      5) Removing one or more of the selected number of the new random predicates from the boosting model in response to input from an operator; and
      6) Repeating the performance of steps 1, 2, 3, 4 and 5 a plurality of times and thereby generating a final iteratively trained boosting model.

19. The method of claim 18, further comprising the step d) of evaluating the final iteratively trained boosting model.

20. A workstation for providing operator input into iteratively training a boosting model, wherein the workstation comprises an interface and a processor, and wherein the processor is configured to perform operations comprising:
   1) Generating a number of new random predicates as binary functions operating on at least one of (i) time sequences of input features or (ii) logical operations on the time sequences of the input features;
   2) Scoring all the new random predicates by weighted information gain with respect to a class label associated with a prediction of the boosting model;
   3) Selecting, from the new random predicates, a number of the new random predicates that are the highest with respect to their weighted information gain scores and adding them to the boosting model;
   4) Computing weights for all the predicates in the boosting model;
   5) Removing one or more of the selected number of the new random predicates from the boosting model in response to input from an operator, wherein the input is received by way of the interface; and
   6) Repeating the performance of steps 1, 2, 3, 4 and 5 a plurality of times and thereby generating a final iteratively trained boosting model.

21. The workstation of claim 20, wherein predicates are defined as at least one of (i) binary functions operating on sequences of features having both a real value component and a time component or (ii) logical operations on sequences of the features.

22. The workstation of claim 20, wherein the operations further comprise the step of graphically representing on the interface a set of predicates added to the boosting model after each of the iterations of step 6).

23. The workstation of claim 20, wherein the step (i) of automatically generating the plurality of additional predicates comprises:
   (a) generating candidate predicates by a pseudo-random algorithm;
   (b) scoring the candidate predicates for weighted information gain in the boosting model; and
   (c) selecting the additional predicates from the candidate predicates based on the scores.

24. The workstation of claim 23, wherein the output of each predicate is a binary value.

25. The workstation of claim 23, wherein each sample in the training data is formatted as a plurality of data items having a tuple format of the type $\{X, x_i, t_i\}$, wherein $x_i$ indicates the value of feature X at a time $t_i$, and i labels the tuple of the sample, and wherein each predicate is defined as a function performed on a plurality of data items of the sample.

26. The workstation according to claim 23, wherein the training data comprises electronic health record data for a plurality of patients.

27. The workstation of claim 23, wherein each predicate is a function of a part of the sample relating to a single corresponding one of the features.

28. The workstation according to claim 23, wherein the features are each associated with a corresponding one of a set of human understandable categories or groups, and step (iii) of displaying a plurality of the set of predicates includes displaying grouped together the predicates which are functions of data relating to features of each category or group.

29. The workstation of claim 23, wherein step (iii) of displaying a plurality of the set of predicates includes displaying a respective weight value of the boosting model.

30. The workstation of claim 23, further comprising evaluating the accuracy of the boosting model in predicting the label using a validation sub-set of the training data.

31. The workstation of claim 23, wherein the rejected one or more of the updated set of predicates are not causally related to a prediction of the boosting model.

32. A computer-implemented method of generating a predictive model from training data, the predictive model being for predicting a label based on input data which, for each of a plurality of features X, indicates a value x of the feature at each of a plurality of times, and the training data comprising a plurality of samples, each sample indicating the value of one or more of the features at each of one of more times and a corresponding label; the method comprising implementing the following steps as instructions with a processor:
- defining a set of predicates, each predicate being a function which generates an output when applied to time sequences of the features or logical combinations of the time sequences of the features;
- generating a boosting model, the boosting model receiving as input the respective outputs of each of the set of predicates when applied to the samples of the training data; and
- performing a plurality of times, the sequence of steps of:
  (i) automatically generating a plurality of additional predicates as binary functions operating on at least one of (i) time sequences of the features or (ii) logical operations on the time sequences of the features;
  (ii) adding the plurality of additional predicates to predicates already in the boosting model to form an updated set of predicates;
  (iii) displaying a plurality of the updated set of predicates; and
  (iv) receiving data input rejecting one or more of the updated set of predicates; and
  (v) removing the rejected one or more predicates from the updated set of predicates.

33. The method of claim 32, wherein the additional predicates comprise at least one of existence predicates which are each indicative of a specific feature taking a value in a specific range at least one time, and count predicates which are each indicative of a specific feature taking a value in a specific range at more than, less than, or equal to a specific number of times C.

* * * * *